United States Patent [19]

Wagner et al.

[11] Patent Number: 5,162,329

[45] Date of Patent: Nov. 10, 1992

[54] DERIVATIVES OF BETA-PICOLINE AND CROP PROTECTION AGENTS CONTAINING THEM

[75] Inventors: Oliver Wagner, Ludwigshafen; Bernhard Zipperer, Dirmstein; Norbert Goetz, Worms; Michael Keil, Freinsheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 704,938

[22] Filed: May 23, 1991

[30] Foreign Application Priority Data

Jun. 7, 1990 [DE] Fed. Rep. of Germany ....... 4018260

[51] Int. Cl.$^5$ .................. A01N 43/40; C07D 213/30; C07D 213/50; C07D 213/53
[52] U.S. Cl. ..................... 514/277; 514/357; 546/330; 546/333; 546/334; 546/338; 546/340; 546/342; 546/346
[58] Field of Search ............... 546/330, 333, 334, 338, 546/340, 342, 346; 514/277, 357

[56] References Cited

U.S. PATENT DOCUMENTS

| | | | |
|---|---|---|---|
| 4,753,947 | 6/1988 | Dorn et al. | 546/344 |
| 4,766,132 | 8/1988 | Kay | 546/330 |
| 4,933,339 | 6/1990 | Sharma | 546/330 |
| 4,999,357 | 3/1991 | Gadras et al. | 546/330 |

OTHER PUBLICATIONS

J. Org. Chem., vol. 43, No. 17, 1978, pp. 3396-3398.

*Primary Examiner*—Marianne M. Cintins
*Assistant Examiner*—John Peabody
*Attorney, Agent, or Firm*—Oblon, Spivak, McClelland, Maier & Neustadt

[57] ABSTRACT

$\beta$-picoline derivatives of the formula

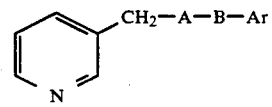

where
A is $CR^1R^2$, $R^1$ and $R^2$ independently of each other are hydrogen, alkyl, alkenyl or alkynyl, or $R^1$ and $R^2$ together form a methylene chain,
B is one of the groups $CH_2$, $CHOR^3$, $CHalR^4$, $C=O$ or $C=N-O-R^5$, $R^3$ being hydrogen, alkyl, haloalkyl, cycloalkyl, alkenyl, acyl, phenyl, benzyl or benzoyl, where the phenyl ring is substituted or unsubstituted, $R^4$ being hydrogen, fluorine, chlorine, bromine or iodine, $R^5$ being hydrogen, alkyl, haloalkyl, cycloalkyl, alkenyl, phenyl or benzyl, the phenyl ring being substituted or unsubstituted,
Ar is a substituted or unsubstituted aryl radical,
their N-oxides and plant-tolerated acid addition salts, and fungicides containing these compounds.

10 Claims, No Drawings

DERIVATIVES OF BETA-PICOLINE AND CROP PROTECTION AGENTS CONTAINING THEM

The present invention relates to β-picoline derivatives and fungicides containing them.

The compound 1-phenyl-3-(3-pyridinyl)-propan-1-one is disclosed in J. Org. Chem. 43 (1978), 3396 and in Arch. Pharm. 307 (1974), 550, but a fungicidal action is not reported.

We have found that β-picoline derivatives of the formula $$\text{pyridine-CH}_2\text{—A—B—Ar} \quad (I)$$

where
A is $CR^1R^2$,
$R^1$ and $R^2$ independently of one another are each hydrogen, $C_1$-$C_5$-alkyl, $C_2$-$C_6$-alkenyl or $C_2$-$C_6$-alkynyl or $R^1$ and $R^2$ together form a methylene chain having from 2 to 6 methylene groups,
B is one of the groups $CH_2$, $CHOR^3$, $CHR^4$, C=O or C=N-O-$R^5$,
$R^3$ is hydrogen, $C_1$-$C_6$-alkyl, $C_1$-$C_6$-haloalkyl, $C_3$-$C_8$-cycloalkyl, $C_3$-$C_6$-alkenyl, $C_2$-$C_6$-acyl, phenyl, benzyl or benzoyl, where the phenyl ring may be unsubstituted or substituted by from one to three substituents from the group consisting of $C_1$-$C_4$-alkyl, $C_1$-$C_4$-alkoxy, $C_1$-$C_4$-haloalkyl, $C_1$-$C_4$-haloalkoxy, halogen, cyano and nitro,
$R^4$ is hydrogen, fluorine, chlorine, bromine or iodine,
$R^5$ is hydrogen, $C_1$-$C_5$-alkyl, $C_1$-$C_6$-haloalkyl, $C_3$-$C_7$-cycloalkyl, $C_3$-$C_6$-alkenyl or aralkyl where the alkyl radical is of 1 to 4 carbon atoms and the aryl radical may be unsubstituted or substituted by from one to three substituents from the group consisting of $C_1$-$C_4$-alkyl, $C_1$-$C_4$-alkoxy, $C_1$-$C_4$-haloalkyl, halogen, cyano and nitro, and Ar is a mononuclear or dinuclear aryl radical which is unsubstituted or monosubstituted to trisubstituted by halogen, $C_1$-$C_5$-alkyl, $C_1$-$C_4$-alkoxy, $C_1$-$C_4$-haloalkyl, $C_1$-$C_4$-haloalkoxy, phenyl, phenoxy, halophenyl, halophenoxy or benzyloxy,
and their N-oxides and plant-tolerated acid addition salts, except for the compound in which A is $CH_2$, B is C=O and Ar is phenyl, have a good fungicidal action, which is better than the action of known active ingredients.

$R^1$ and $R^2$ independently of one another are each, for example, hydrogen, methyl, ethyl, n-propyl, isopropyl, n-butyl, isobutyl, tert-butyl, n-pentyl, neopentyl, isopentyl, n-hexyl, allyl, 2-methylallyl, 3-methylallyl, 3,3-dimethylallyl or propargyl. The radicals $CR^1R^2$ in which $R^1$ is not hydrogen, in particular the radicals in which $R^1$ and $R^2$ are not hydrogen, are preferred.

$R^1$ and $R^2$ together may furthermore, together with the carbon atom of which they are substituents, form a cycloalkyl ring of 3 to 7 carbon atoms which contains from 2 to 6 methylene groups.

$R^3$ is, for example, hydrogen, methyl, ethyl, n-propyl, isopropyl, n-butyl, isobutyl, tert-butyl, n-pentyl, neopentyl, isopentyl, n-hexyl, cyclopropyl, cyclopentyl, cyclohexyl, cycloheptyl, cyclooctyl, allyl, 2-methylallyl, 3-methylallyl, 3,3-dimethylallyl, propargyl, trifluoromethyl, chloromethyl, dichloromethyl, trichloromethyl, bromomethyl, 2-bromoethyl, 2-chloroethyl, 3-bromopropyl, 4-bromobutyl, phenyl, mono-, di- or trimethylphenyl, 4-tert-butylphenyl, mono-, di- or trimethoxyphenyl, trifluoromethylphenyl, fluorophenyl, mono-, di- or trichlorophenyl, mono- or dinitrophenyl, cyanophenyl, mono-, di- or tribenzyl, 4-tert-butylphenyl, mono-, di- or trimethoxyb-enzyl, trifluoromethylbenzyl, fluorobenzyl, mono-, di- or trichlorobenzyl, mono- or dinitrobenzyl, cyanobenzyl, mono-, di- or trimethylbenzoyl, 4-tert-butylbenzoyl, mono-, di- or trimethoxybenzoyl, trifluoromethylbenzoyl, fluorobenzoyl, mono-, di- or trichlorobenzoyl, mono- or dinitrobenzoyl, cyanobenzoyl, acetyl, propionyl, butyryl, pentanoyl or hexanoyl $R^5$ is, for example, hydrogen, methyl, ethyl, n-propyl, isopropyl, n-butyl, isobutyl, tert-butyl, n-pentyl, neopentyl, isopentyl, n-hexyl, cyclopropyl, cyclobutyl, cyclopentyl, cyclohexyl, cycloheptyl, cyclooctyl, allyl, 2-methylallyl, 3-methylallyl, 3,3-dimethylally, propargyl, trifluoromethyl, chloromethyl, dichloromethyl, trichloromethyl, bromomethyl, 2-bromcethyl, 2-chloroethyl, 3-bromopropyl, 4-bromobutyl, phenyl, mono-, di- or trimethylphenyl, 4-tert-butylphenyl, mono-, di- or trimethoxyphenyl, trifluoromethylphenyl, fluorophenyl, mono-, di- or trichlorophenyl, mono- or dinitrophenyl, cyanophenyl, mono-, di- or trimethylbenzyl, 4-tert-butylbenzyl, mono-, di- or trimethoxybenzyl, trifluoromethylbenzyl, fluorobenzyl, mono-, di- or trichlorobenzyl, mono- or dinitrobenzyl or cyanobenzyl and Ar is, for example, phenyl, 2-methylphenyl, 3-methylphenyl, 4-methylphenyl, 2,4-dimethylphenyl, 2,6-dimethylphenyl, 2,4,6-trimethylphenyl, 4-isopropylphenyl, 4-tert-butylphenyl, 1-naphthyl, 2-naphthyl, 4-biphenyl, 2-fluorophenyl, 3-fluorophenyl, 4-fluorophenyl, 2,4-difluorophenyl, 2-chlorophenyl, 3-chlorophenyl, 4-chlorophenyl, 2,4-dichlorophenyl, 3,4-dichlorophenyl, 2,4,6-trichloropheny-1,2-chloro-4-fluoropheny1,2-trifluoromethylphenyl, 3-trifluoromethylphenyl, 4-trifluoromethylphenyl, 2-, 3- or 4-methoxyphenyl, 3,4-dimethoxyphenyl, 4-trifluoromethoxyphenyl, 4-tetrafluoroethoxyphenyl- 2-chloro-1,4-phenoxypheny1,4-(4,-chlorophenoxy)-phenyl or 4-benzyloxyphenyl.

The compounds of the formula I may have two or more centers of asymmetry and can therefore occur in two or more diastereomeric forms, which can be separated by known methods, for example by chromatography or crystallization. The present invention relates both to the pure diastereomers and to mixtures thereof and to their use as fungicides.

The β-picoline derivatives can be prepared by a method in which an aldehyde of the formula II $$\text{pyridine-CH}_2\text{—A—CHO} \quad (II)$$

where A has the abovementioned meanings, is reacted with an organometallic compound of the formula III $$\text{Ar-M} \quad (III)$$

where M is lithium or one of the radicals MgCl, MgBr or MgI and Ar has the abovementioned meanings. It is advantageous initially to take the organometallic compound of the formula III in an inert solvent, preferably an ether, such as diethyl ether or tetrahydrofuran, at from 0 to 80° C., preferably from 0 to 20° C., and to add the aldehyde of the formula II, if necessary dissolved in a diluent.

The organometallic compounds of the formula III are generally known. The aldehydes of the formula II where A is CH₂ or CH(CH₃) are disclosed in J. Org. Chem. 43 (1978), 3396 and 2947. The other aldehydes of the formula II where A has the abovementioned meanings are novel. They can be prepared, for example, by alkylating an aldehyde of the formula IV

H—A—CHO  (IV)

where A has the abovementioned meanings with the exception of CH₂ and CH(CH₃), with 3-chloromethylpyridine produced in situ, in the presence of a base. 3-Chloromethylpyridine is unstable and tends to form a resin at as low as room temperature (cf. for example CA 47, 8068e). A 3-chloromethylpyridine liberated in situ from the hydrochloride is a suitable reagent for the alkylation of aldehydes.

The direct alpha-alkylation of aldehydes takes place, as a rule, with only poor yields, and the same applies to the enamines derived from the aldehydes (cf. for example G. Opitz et al., Liebigs Ann. Chem. 649 (1961), 36). A simple preparative method is the alphaalkylation of aldehydes under phase transfer catalysis. This process can be carried out as a solid/liquid variant in a two-phase system consisting of solid sodium hydroxide and a lipophilic organic solvent (cf. H. K. Dietl and K. C. Brannock, Tetrahedron Lett. 1273 (1973); E. Buschmann and B. Zeeh, Liebigs Ann. Chem. 1585 (1979)). Particularly advantageous here is a liquid/liquid variant in which the sodium hydroxide solution and an organic, water immiscible solvent and a suitable phase transfer catalyst are initially taken and the aldehyde IV, if necessary dissolved in a diluent, and the 3-chloromethylpyridine hydrochloride, if necessary in the form of an aqueous solution, are metered in. Examples of suitable organic phases are hydrocarbons, such as petroleum ether, cyclohexane, benzene, toluene, xylene or chlorohydrocarbons, such as dichloromethane or 1,2-dichloroethane. For example, crown ethers or quaternary ammonium salts, preferably tetra-n-butylammonium salts, benzyltriethylammonium salts or methyltrioctylammonium salts, can be used as phase transfer catalysts. The reaction is preferably carried out at from 0 to 100° C., in particular from 20 to 80° C. In another process for the preparation of aldehydes of the formula II, an α,β-unsaturated aldehyde of the formula

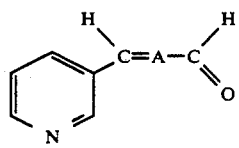

(V)

where A is C-(C₁-C₆-alkyl), is hydrogenated with hydrogen in the presence of a suitable catalyst. The aldehydes of the formula V are novel. They can be prepared by a method in which the aldehyde

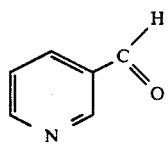

is reacted with an aldehyde

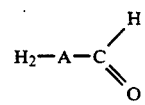

(similarly to European Patent 298, 380).

The processes for carrying out the oxidation of the alcohols of the general formula I (B=CHOH) are known from the literature (cf. for example Houben-Weyl, Methoden der organischen Chemie, Volume VII/2a, Ketone Part 1, page 699 et seq.). A preferred process is the oxidation with dimethyl sulfoxide in the presence of suitable reagents, for example oxalyl chloride/triethylamine. Suitable diluents are inert organic solvents, for example hydrocarbons, such as petroleum ether, cyclohexane, benzene or chlorohydrocarbons, such as dichloromethane, 1,2-dichloroethane or chloroform, or ethers, eg. diethyl ether, tetrahydrofuran or dioxane. The reaction is carried out at from −80 to 50° C., preferably from −70 to −10° C.

The chlorides of the general formula I where B is H—C—Cl are obtainable from the corresponding hydroxy compounds by methods known from the literature (cf. for example Houben-Weyl, Methoden der organischen Chemie, Volume V/3, Halogenverbindungen).

The reaction of thionyl chloride with the alcohols is a preferably used process. Suitable diluents are inert solvents, for example hydrocarbons, such as petroleum ether, cyclohexane, benzene, toluene or xylene. The reaction is carried out at from 40 to 150° C., preferably 80° C., in the presence or absence of a catalyst. Examples of suitable catalysts are dimethylformamide and tertiary amines, such as triethylamine, N,N-dimethylaniline or piperidine.

The oxime ethers of the general formula I where B is C=R⁵ and R⁵ has the meanings stated in the claim are obtainable by conventional processes (cf. Houben-Weyl, Methoden der organischen Chemie, X, 4/55).

A preferably used process is the reaction of the ketones of the general formula I where B is C=O and a hydroxylamine in a suitable diluent and suitable reagents. Suitable diluents are inert organic solvents, for example hydrocarbons, such as petroleum ether, cyclohexane or benzene, or chlorohydrocarbons, such as dichloromethane, 1,2-dichloroethane or chloroform, ethers, eg. diethyl ether, tetrahydrofuran or dioxane, nitriles, such as acetonitrile or propionitrile, and alcohols, such as methanol, ethanol or n-butanol.

Suitable reaction assistants are all conventional inorganic and organic bases, for example alkali metal hydroxides, such as sodium hydroxide or potassium hydroxide, alkali metal alcoholates, such as sodium methylate, sodium ethylate or potassium tert-butylate, alkali metal carbonates, such as sodium carbonate, potassium carbonate, sodium bicarbonate or potassium bicarbonate, and tertiary amines, such as triethylamine, N,N-dimethylaniline or piperidine.

The reaction is carried out at from 20 to 150° C., preferably from 50 to 130° C.

The N-oxides can be prepared by oxidizing the β-picoline derivatives of the formula I.

Plant-tolerated acid addition salts are salts of the β-picoline derivatives of the formula I with inorganic or organic acids, for example sulfuric acid, phosphoric acid, acetic acid, propionic acid, oxalic acid, phenylsulfonic acid or dodecylbenzenesulfonic acid.

The methods and Examples which follow illustrate the preparation of the intermediates and of the novel compounds.

Method 1

2-(Pyrid-3-ylmethyl)-hexanol

A mixture of 21 g (0.11 mol) of 2-butyl-3-pyridylpropenal, 120 ml of methanol, 10 g of N-methylmorpholine and 6 g of a hydrogenation catalyst (10% of Pd and 5% of $Pr_2O_3$ on $Al_2O_3$) is hydrogenated at 75° C. and 75 bar hydrogen pressure in a 0.3 l stirred autoclave until the pressure remains constant. The solution is filtered under suction over silica gel, the filtrate is evaporated down under reduced pressure and the residue is purified by distillation.

Yield: 24.1 g (56.8%)

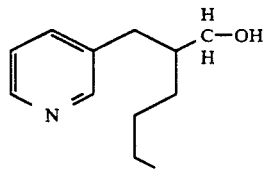

Method 2

2-(Pyrid-3-ylmethyl)-hexanal 23 g (0.132 mol) of dimethy sulfoxide in 120 ml of $CH_2Cl_2$ are added dropwise in the course of one hour to 17 g (0.132 mol) of oxalyl chloride in 280 ml of $CH_2Cl_2$ at −60° C. Thereafter, 23 g (0.12 mol) of 2-(pyrid-3-ylmethyl)-hexanol in 240 ml of $CH_2Cl_2$ are slowly added, followed by 62 g of triethylamine after 30 minutes.

The mixture is allowed to reach room temperature (RT, 20° C.) slowly and 350 ml of $H_2O$ are added. The aqueous phase is extracted with 3×300 ml of $CH_2Cl_2$ and the combined methylene chloride phases are washed with $NaHCO_3$ solution. Drying is carried out over $Na_2SO_4$, the solvent is evaporated off and the residue is then subjected to distillation. 8.2 g (36%) of the title compound (118–120° C., 0.7 mmHg) are obtained.

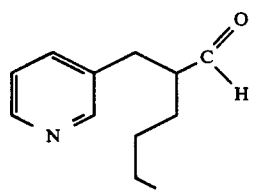

Method 3

2-Ethyl-2-(pyrid-3-ylmethyl)-butanal

A solution of 98.4 g (0.6 mol) of β-picoline chloride hydrochloride and 66 g (0.66 mol) of 2-ethylbutanal in 600 ml of toluene is added dropwise in the course of 3 hours to a mixture of 450 ml of toluene, 600 ml of 30% strength by weight NaOH (4.5 mol) and 7.5 g of tetrabutylammonium iodide at 80° C.

Stirring is then carried out for a further 3 hours at this temperature, the mixture is cooled and 1,000 ml of toluene are then added. The organic phase is separated off, washed three times with water, dried and evaporated down.

Distillation (128–132° C./2 mmHg) gives 56 g (49%) of the title compound.

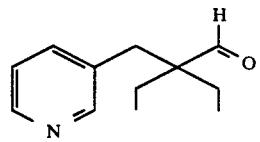

EXAMPLE 1

2-Ethyl-1-(4-fluorophenyl)-2-(pyrid-3-ylmethyl)-butan-1-ol 20.4 g (0.116 mol) of 4-fluorobromobenzene in 250 ml of tetrahydrofuran are added dropwise to 2.8 g of magnesium turnings (0.166 mol) and stirring is carried out for half an hour at RT. 11 g (0.058 mol) of 2-ethyl-2-(pyrid-3-ylmethyl)-butanal in 100 ml of tetrahydrofuran are then slowly added dropwise. After 2 hours, the mixture is poured onto ice water and brought to pH 8 with saturated $NH_4Cl$ solution. It is extracted with ether, the organic phase is washed with water and dried over $Na_2SO_4$ and the solvent is then evaporated off. 8 g (48%) of the title compound are obtained as a viscous oil (compound No. 70 in the Table).

EXAMPLE 2

2Ethyl-1-(4-fluorophenyl)-2-(pyrid-30-0ylmethyl)-butan-1-one 22.5 g (0.288 mol) of dimethyl sulfoxide in 50 ml of methylene chloride are added dropwise to 18.6 g (0.144 mol) of oxalyl chloride in 200 ml of $CH_2Cl_2$ at −60° C. The reaction is allowed to continue for 5 minutes at −60° C.

33 g (0.115 mol) of 2-ethyl-1-(4-fluorophenyl)-2-(pyrid-3-ylmethyl)-butanol in 100 ml of $CH_2Cl_2$ are then slowly added and, after 15 minutes, 58.2 g (0.576 mol) of triethylamine are introduced. The mixture is allowed to reach RT slowly, 350 ml of water are added, the aqueous phase is extracted with 3×200 ml of $CH_2Cl_2$ and the combined organic phases are dried over $Na_2SO_4$. After the solvent has been evaporated off, the title compound is obtained in a yield of 49% (compound No. 331).

EXAMPLE 3

1-Chloro-2-ethyl-1-phenyl-2-(pyrid-3-ylmethyl)-butane 13.3 g (0.11 mol) of $SOCl_2$ are added dropwise, at 80° C., to 5 g (0.018 mol) of 2-ethyl-1-phenyl-2-(pyrid-3-ylmethyl)-butanol in 100 ml of toluene and a catalytic amount (0.1 g) of dimethylformamide, and the mixture is left for 5 hours at this temperature. The mixture is cooled, poured onto ice water and then rendered alkaline with 30% strength NaOH solution. The aqueous phase is extracted with three times 50 ml of tert-butyl methyl ether and the combined organic phases are dried over $MgSO_4$. After the solvent has been evaporated off, the residue is chromatographed over silica gel (1 : 1 toluene/ethyl acetate). 2.07 g (yield 40%) of the title compound are obtained as a viscous yellow oil (compound No. 581).

The compounds listed in the Table below can be prepared in a similar manner.

TABLE

| No. | A | B | Ar | Phys. data IR, cm$^{-1}$ |
|---|---|---|---|---|
| 1 | C(CH$_3$)$_2$ | CHOH | Phenyl | oil 2963, 1449, 1424, 1361, 1059, 1045 |
| 2 | C(CH$_3$)$_2$ | CHOH | 2-Methylphenyl | 107–110° C. |
| 3 | C(CH$_3$)$_2$ | CHOH | 4-Methylphenyl | oil 3146, 1474, 1426, 1069, 1045, 824 |
| 4 | C(CH$_3$)$_2$ | CHOH | 2,4-Dimethylphenyl | |
| 5 | C(CH$_3$)$_2$ | CHOH | 2,6-Diemthylphenyl | |
| 6 | C(CH$_3$)$_2$ | CHOH | 2,4,6-Trimethylphenyl | 155–157° C. |
| 7 | C(CH$_3$)$_2$ | CHOH | 4-tert. Butylphenyl | 144–146° C. |
| 8 | C(CH$_3$)$_2$ | CHOH | 1-Naphtyl | |
| 9 | C(CH$_3$)$_2$ | CHOH | 2-Napthyl | |
| 10 | C(CH$_3$)$_2$ | CHOH | 4-Biphenyl | |
| 11 | C(CH$_3$)$_2$ | CHOH | 2-Fluorophenyl | |
| 12 | C(CH$_3$)$_2$ | CHOH | 4-Fluorophenyl | oil 3200, 2966, 2871, 1602, 1508, 1424 |
| 13 | C(CH$_3$)$_2$ | CHOH | 2,4-Difluorophenyl | |
| 14 | C(CH$_3$)$_2$ | CHOH | 2-Chlorophenyl | |
| 15 | C(CH$_3$)$_2$ | CHOH | 3-Chlorophenyl | |
| 16 | C(CH$_3$)$_2$ | CHOH | 4-Chlorophenyl | oil 3200, 2966, 2934, 2870, 1486, 1424 |
| 17 | C(CH$_3$)$_2$ | CHOH | 2,4-Dichlorophenyl | oil 3300, 2967, 1587, 1467, 717 |
| 18 | C(CH$_3$)$_2$ | CHOH | 3,4-Dichlorophenyl | |
| 19 | C(CH$_3$)$_2$ | CHOH | 2-Chloro-4-fluorophenyl | |
| 20 | C(CH$_3$)$_2$ | CHOH | 2-Trifluoromethylphenyl | |
| 21 | C(CH$_3$)$_2$ | CHOH | 4-Trifluoromethylphenyl | |
| 22 | C(CH$_3$)$_2$ | CHOH | 4-Methoxyphenyl | oil 3250, 2961, 1610, 1511, 1247 |
| 23 | C(CH$_3$)$_2$ | CHOH | 3,4-Dimethoxyphenyl | |
| 24 | C(CH$_3$)$_2$ | CHOH | 4-Tetrafluoroethoxyphenyl | |
| 25 | C(CH$_3$)$_2$ | CHOH | 4-Trifluoromethoxyphenyl | |
| 26 | C(CH$_3$)$_2$ | CHOH | 2-Chloro-4-(4'-chlorophenoxy)phenyl | |
| 27 | C(CH$_3$)$_2$ | CHOH | 4-Phenoxyphenyl | |
| 28 | C(CH$_3$)$_2$ | CHOH | 4-(4'-Chlorophenoxy)phenyl | |
| 29 | C(CH$_3$)$_2$ | CHOH | 4-Benzyloxyphenyl | |
| 30 | C(CH$_3$)(CH$_2$CH$_3$) | CHOH | Phenyl | oil 3200, 2964, 2936, 2877, 1463, 1452 |
| 31 | C(CH$_3$)(CH$_2$CH$_3$) | CHOH | 2-Methylphenyl | |
| 32 | C(CH$_3$)(CH$_2$CH$_3$) | CHOH | 4-Methylphenyl | oil 3200, 2964, 2936, 2877, 1478, 1463, 1424 |
| 33 | C(CH$_3$)(CH$_2$CH$_3$) | CHOH | 2,4-Dimethylphenyl | |
| 34 | C(CH$_3$)(CH$_2$CH$_3$) | CHOH | 2,6-Dimethylphenyl | |
| 35 | C(CH$_3$)(CH$_2$CH$_3$) | CHOH | 2,4,6-Trimethylphenyl | |
| 36 | C(CH$_3$)(CH$_2$CH$_3$) | CHOH | 4-tert. Butylphenyl | |
| 37 | C(CH$_3$)(CH$_2$CH$_3$) | CHOH | 1-Naphthyl | |
| 38 | C(CH$_3$)(CH$_2$CH$_3$) | CHOH | 2-Naphthyl | |
| 39 | C(CH$_3$)(CH$_2$CH$_3$) | CHOH | 4-Biphenyl | |
| 40 | C(CH$_3$)(CH$_2$CH$_3$) | CHOH | 2-Fluorophenyl | |
| 41 | C(CH$_3$)(CH$_2$CH$_3$) | CHOH | 4-Fluorophenyl | oil 3200, 2965, 2937, 1602, 1508, 1424 |
| 42 | C(CH$_3$)(CH$_2$CH$_3$) | CHOH | 2,4-Difluorophenyl | |
| 43 | C(CH$_3$)(CH$_2$CH$_3$) | CHOH | 2-Chlorophenyl | |
| 44 | C(CH$_3$)(CH$_2$CH$_3$) | CHOH | 3-Chlorophenyl | |
| 45 | C(CH$_3$)(CH$_2$CH$_3$) | CHOH | 4-Chlorophenyl | oil 3190, 2965, 2936, 2877, 1486, 1464 |
| 46 | C(CH$_3$)(CH$_2$CH$_3$) | CHOH | 2,4-Dichlorophenyl | |
| 47 | C(CH$_3$)(CH$_2$CH$_3$) | CHOH | 3,4-Dichlorophenyl | |
| 48 | C(CH$_3$)(CH$_2$CH$_3$) | CHOH | 2-Chloro-4-fluorophenyl | |
| 49 | C(CH$_3$)(CH$_2$CH$_3$) | CHOH | 2-Trifluoromethylphenyl | |
| 50 | C(CH$_3$)(CH$_2$CH$_3$) | CHOH | 4-Trifluoromethylphenyl | |
| 51 | C(CH$_3$)(CH$_2$CH$_3$) | CHOH | 4-Methoxyphenyl | |
| 52 | C(CH$_3$)(CH$_2$CH$_3$) | CHOH | 3,4-Dimethoxyphenyl | |
| 53 | C(CH$_3$)(CH$_2$CH$_3$) | CHOH | 4-Tetrafluoroethoxyphenyl | |
| 54 | C(CH$_3$)(CH$_2$CH$_3$) | CHOH | 4-Trifluoromethoxyphenyl | |
| 55 | C(CH$_3$)(CH$_2$CH$_3$) | CHOH | 2-Chloro-4-(4'-chlorophenoxy)phenyl | |
| 56 | C(CH$_3$)(CH$_2$CH$_3$) | CHOH | 4-Phenoxyphenyl | |
| 57 | C(CH$_3$)(CH$_2$CH$_3$) | CHOH | 4-(4'-Chlorophenoxy)phenyl | |
| 58 | C(CH$_3$)(CH$_2$CH$_3$) | CHOH | 4-Benzyloxyphenyl | |
| 59 | C(CH$_2$CH$_3$)$_2$ | CHOH | Phenyl | oil 3203, 2963, 2935, 2879, 1452, 1424 |
| 60 | C(CH$_2$CH$_3$)$_2$ | CHOH | 2-Methylphenyl | oil 3320, 2963, 1425, 1030, 758, 718 |
| 61 | C(CH$_2$CH$_3$)$_2$ | CHOH | 4-Methylphenyl | oil 2965, 2936, 2879, 1478, 1455, 1424 |
| 62 | C(CH$_2$CH$_3$)$_2$ | CHOH | 2,4-Dimethylphenyl | |
| 63 | C(CH$_2$CH$_3$)$_2$ | CHOH | 2,6-Dimethylphenyl | |
| 64 | C(CH$_2$CH$_3$)$_2$ | CHOH | 2,4,6-Trimethylphenyl | 161–164° C. |
| 65 | C(CH$_2$CH$_3$)$_2$ | CHOH | 4-tert. Butylphenyl | |
| 66 | C(CH$_2$CH$_3$)$_2$ | CHOH | 1-Naphthyl | |
| 67 | C(CH$_2$CH$_3$)$_2$ | CHOH | 2-Naphthyl | |
| 68 | C(CH$_2$CH$_3$)$_2$ | CHOH | 4-Biphenyl | |
| 69 | C(CH$_2$CH$_3$)$_2$ | CHOH | 2-Fluorophenyl | |
| 70 | C(CH$_2$CH$_3$)$_2$ | CHOH | 4-Fluorophenyl | oil 3200, 2966, 2937, 2879, 1602, 1507 |
| 71 | C(CH$_2$CH$_3$)$_2$ | CHOH | 2,4-Difluorophenyl | |
| 72 | C(CH$_2$CH$_3$)$_2$ | CHOH | 2-Chlorophenyl | |
| 73 | C(CH$_2$CH$_3$)$_2$ | CHOH | 3-Chlorophenyl | |
| 74 | C(CH$_2$CH$_3$)$_2$ | CHOH | 4-Chlorophenyl | oil 3200, 2966, 2937, 2878, 1487, 1424 |
| 75 | C(CH$_2$CH$_3$)$_2$ | CHOH | 2,4-Dichlorophenyl | mp. 142–144° C. |
| 76 | C(CH$_2$CH$_3$)$_2$ | CHOH | 3,4-Dichlorophenyl | |
| 77 | C(CH$_2$CH$_3$)$_2$ | CHOH | 2-Chloro-4-fluorophenyl | |

TABLE-continued

| No. | A | B | Ar | Phys. data IR, cm$^{-1}$ |
|---|---|---|---|---|
| 78 | C(CH$_2$CH$_3$)$_2$ | CHOH | 2-Trifluoromethylphenyl | |
| 79 | C(CH$_2$CH$_3$)$_2$ | CHOH | 4-Trifluoromethylphenyl | |
| 80 | C(CH$_2$CH$_3$)$_2$ | CHOH | 4-Methoxyphenyl | oil 3200, 2963, 1510, 1246, 1031, 717 |
| 81 | C(CH$_2$CH$_3$)$_2$ | CHOH | 3,4-Dimethoxyphenyl | |
| 82 | C(CH$_2$CH$_3$)$_2$ | CHOH | 4-Tetrafluoroethoxyphenyl | |
| 83 | C(CH$_2$CH$_3$)$_2$ | CHOH | 4-Trifluoromethoxyphenyl | |
| 84 | C(CH$_2$CH$_3$)$_2$ | CHOH | 2-Chloro-4-(4'-chlorophenoxy)phenyl | |
| 85 | C(CH$_2$CH$_3$)$_2$ | CHOH | 4-Phenoxyphenyl | |
| 86 | C(CH$_2$CH$_3$)$_2$ | CHOH | 4-(4'-Chlorophenoxy)phenyl | |
| 87 | C(CH$_2$CH$_3$)$_2$ | CHOH | 4-Benzyloxyphenyl | |
| 88 | Cyclopropylene | CHOH | Phenyl | oil 3231, 3027, 1424, 1028, 715, 702 |
| 89 | Cyclopropylene | CHOH | 2-Methylphenyl | |
| 90 | Cyclopropylene | CHOH | 4-Methylphenyl | oil 3238, 2921, 1424, 1044, 820, 716 |
| 91 | Cyclopropylene | CHOH | 2,4-Dimethylphenyl | |
| 92 | Cyclopropylene | CHOH | 2,6-Dimethylphenyl | |
| 93 | Cyclopropylene | CHOH | 2,4,6-Trimethylphenyl | |
| 94 | Cyclopropylene | CHOH | 4-tert. Butylphenyl | |
| 95 | Cyclopropylene | CHOH | 1-Naphthyl | |
| 96 | Cyclopropylene | CHOH | 2-Naphthyl | |
| 97 | Cyclopropylene | CHOH | 4-Biphenyl | |
| 98 | Cyclopropylene | CHOH | 4-Fluorophenyl | |
| 99 | Cyclopropylene | CHOH | 4-Fluorophenyl | oil 3200, 2940, 1508, 1221, 838 |
| 100 | Cyclopropylene | CHOH | 2,4-Difluorophenyl | |
| 101 | Cyclopropylene | CHOH | 2-Chlorophenyl | |
| 102 | Cyclopropylene | CHOH | 3-Chlorophenyl | |
| 103 | Cyclopropylene | CHOH | 4-Chlorophenyl | oil 3200, 2924, 1425, 1014, 717 |
| 104 | Cyclopropylene | CHOH | 2,4-Dichlorophenyl | |
| 105 | Cyclopropylene | CHOH | 3,4-Dichlorophenyl | |
| 106 | Cyclopropylene | CHOH | 2-Chloro-4-fluorophenyl | |
| 107 | Cyclopropylene | CHOH | 2-Trifluoromethylphenyl | |
| 108 | Cyclopropylene | CHOH | 4-Trifluoromethylphenyl | |
| 109 | Cyclopropylene | CHOH | 4-Methoxyphenyl | |
| 110 | Cyclopropylene | CHOH | 3,4-Dimethoxyphenyl | |
| 111 | Cyclopropylene | CHOH | 4-Tetrafluoroethoxyphenyl | |
| 112 | Cyclopropylene | CHOH | 4-Trifluoromethoxyphenyl | |
| 113 | Cyclopropylene | CHOH | 2-Chloro-4-(4'-chlorophenoxy)phenyl | |
| 114 | Cyclopropylene | CHOH | 4-Phenoxyphenyl | |
| 115 | Cyclopropylene | CHOH | 4-(4'-Chlorophenoxy)phenyl | |
| 116 | Cyclopropylene | CHOH | 4-Benzyloxyphenyl | |
| 117 | Cyclopentylene | CHOH | Phenyl | oil 3211, 2953, 2869, 1478, 1451, 1424 |
| 118 | Cyclopentylene | CHOH | 2-Methylphenyl | oil 3225, 2954, 1442, 1031, 740, 719 |
| 119 | Cyclopentylene | CHOH | 4-Methylphenyl | oil 3225, 2952, 2869, 1478, 1451, 1424 |
| 120 | Cyclopentylene | CHOH | 2,4-Dimethylphenyl | |
| 121 | Cyclopentylene | CHOH | 2,6-Dimethylphenyl | |
| 122 | Cyclopentylene | CHOH | 2,4,6-Trimethylphenyl | 141–142° C. |
| 123 | Cyclopentylene | CHOH | 4-tert. Butylphenyl | |
| 124 | Cyclopentylene | CHOH | 1-Naphthyl | |
| 125 | cyclopentylene | CHOH | 2-Naphthyl | |
| 126 | Cyclopentylene | CHOH | 4-Biphenyl | |
| 127 | Cyclopentylene | CHOH | 2-Fluorophenyl | |
| 128 | Cyclopentylene | CHOH | 4-Fluorophenyl | oil 3200, 2954, 2871, 1603, 1507, 1425 |
| 129 | Cyclopentylene | CHOH | 2,4-Difluorophenyl | |
| 130 | Cyclopentylene | CHOH | 2-Chlorophenyl | |
| 131 | Cyclopentylene | CHOH | 3-Chlorophenyl | |
| 132 | Cyclopentylene | CHOH | 4-Chlorophenyl | oil 2954, 2870, 1484, 1090, 1046, 1030 |
| 133 | Cyclopentylene | CHOH | 2,4-Dichlorophenyl | mp. 150–151° C. 3270, 2952, 2872, 2706, 2625, 1541 |
| 134 | Cyclopentylene | CHOH | 3,4-Dichlorophenyl | |
| 135 | Cyclopentylene | CHOH | 2-Chloro-4-fluorophenyl | |
| 136 | Cyclopentylene | CHOH | 2-Trifluoromethylphenyl | |
| 137 | Cyclopentylene | CHOH | 4-Trifluoromethylphenyl | |
| 138 | Cyclopentylene | CHOH | 4-Methoxyphenyl | 91–93° C. |
| 139 | Cyclopentylene | CHOH | 3,4-Dimethoxyphenyl | |
| 140 | Cyclopentylene | CHOH | 4-Tetrafluoroethoxyphenyl | |
| 141 | Cyclopentylene | CHOH | 4-Trifluoromethoxyphenyl | |
| 142 | Cyclopentylene | CHOH | 2-Chloro-4-(4'-chlorophenoxy)phenyl | |
| 143 | Cyclopentylene | CHOH | 4-Phenoxyphenyl | |
| 144 | Cyclopentylene | CHOH | 4-(4'-Chlorophenoxy)phenyl | |
| 145 | Cyclopentylene | CHOH | 4-Benzyloxyphenyl | |
| 146 | Cyclohexylene | CHOH | Phenyl | oil 2933, 2860, 1454, 1424, 1067, 1042 |
| 147 | Cyclohexylene | CHOH | 2-Methylphenyl | oil 3200, 2934, 1458, 1069, 737, 719 |
| 148 | Cyclohexylene | CHOH | 4-Methylphenyl | oil 2933, 2860, 1456, 1423, 1069, 1042 |
| 149 | Cyclohexylene | CHOH | 2,4-Dimethylphenyl | |
| 150 | Cyclohexylene | CHOH | 2,6-Dimethylphenyl | |
| 151 | Cyclohexylene | CHOH | 2,4,6-Trimethylphenyl | 164° C. |
| 152 | Cyclohexylene | CHOH | 4-tert. Butylphenyl | 167–169° C. |
| 153 | Cyclohexylene | CHOH | 1-Naphthyl | |
| 154 | Cyclohexylene | CHOH | 2-Naphthyl | |
| 155 | Cyclohexylene | CHOH | 4-Biphenyl | |
| 156 | Cyclohexylene | CHOH | 2-Fluorophenyl | |
| 157 | Cyclohexylene | CHOH | 4-Fluorophenyl | mp. 133–135° C. 3264, 2928, 2862, 1507, 1453, 1428, 1222 |

TABLE-continued

| No. | A | B | Ar | Phys. data IR, cm$^{-1}$ |
|---|---|---|---|---|
| 158 | Cyclohexylene | CHOH | 2,4-Difluorophenyl | |
| 159 | Cyclohexylene | CHOH | 2-Chlorophenyl | |
| 160 | Cyclohexylene | CHOH | 3-Chlorophenyl | |
| 161 | Cyclohexylene | CHOH | 4-Chlorophenyl | oil 3152, 2931, 1480, 1427, 1076, 717 |
| 162 | Cyclohexylene | CHOH | 2,4-Dichlorophenyl | 140–141° C. |
| 163 | Cyclohexylene | CHOH | 3,4-Dichlorophenyl | |
| 164 | Cyclohexylene | CHOH | 2-Chloro-4-fluorophenyl | |
| 165 | Cyclohexylene | CHOH | 2-Trifluoromethylphenyl | |
| 166 | Cyclohexylene | CHOH | 4-Trifluoromethylphenyl | |
| 167 | Cyclohexylene | CHOH | 4-Methoxyphenyl | 126–129° C. |
| 168 | Cyclohexylene | CHOH | 3,4-Dimethoxyphenyl | |
| 169 | Cyclohexylene | CHOH | 4-Tetrafluoroethoxyphenyl | |
| 170 | Cyclohexylene | CHOH | 4-Trifluoromethoxyphenyl | |
| 171 | Cyclohexylene | CHOH | 2-Chloro-4-(4'-chlorophenoxy)phenyl | |
| 172 | Cyclohexylene | CHOH | 4-Phenoxyphenyl | |
| 173 | Cyclohexylene | CHOH | 4-(4'-Chlorophenoxy)phenyl | |
| 174 | Cyclohexylene | CHOH | 4-Benzyloxyphenyl | |
| 175 | C(CH$_3$)(C$_3$H$_7$) | CHOH | Phenyl | oil 2958, 2933, 2871, 1452, 1424, 1068 |
| 176 | C(CH$_3$)(C$_3$H$_7$) | CHOH | 2-Methylphenyl | |
| 177 | C(CH$_3$)(C$_3$H$_7$) | CHOH | 4-Methylphenyl | oil 2958, 2933, 2870, 1467, 1456, 1424 |
| 178 | C(CH$_3$)(C$_3$H$_7$) | CHOH | 2,4-Dimethylphenyl | |
| 179 | C(CH$_3$)(C$_3$H$_7$) | CHOH | 2,6-Dimethylphenyl | |
| 180 | C(CH$_3$)(C$_3$H$_7$) | CHOH | 2,4,6-Trimethylphenyl | |
| 181 | C(CH$_3$)(C$_3$H$_7$) | CHOH | 4-tert. Butylphenyl | |
| 182 | C(CH$_3$)(C$_3$H$_7$) | CHOH | 1-Naphthyl | |
| 183 | C(CH$_3$)(C$_3$H$_7$) | CHOH | 2-Naphthyl | |
| 184 | C(CH$_3$)(C$_3$H$_7$) | CHOH | 4-Biphenyl | |
| 185 | C(CH$_3$)(C$_3$H$_7$) | CHOH | 2-Fluorophenyl | |
| 186 | C(CH$_3$)(C$_3$H$_7$) | CHOH | 4-Fluorophenyl | oil 2959, 2934, 2871, 1508, 1425, 1223 |
| 187 | C(CH$_3$)(C$_3$H$_7$) | CHOH | 2,4-Difluorophenyl | |
| 188 | C(CH$_3$)(C$_3$H$_7$) | CHOH | 2-Chlorophenyl | |
| 189 | C(CH$_3$)(C$_3$H$_7$) | CHOH | 3-Chlorophenyl | |
| 190 | C(CH$_3$)(C$_3$H$_7$) | CHOH | 4-Chlorophenyl | oil 2958, 2933, 2871, 1486, 1424, 1090 |
| 191 | C(CH$_3$)(C$_3$H$_7$) | CHOH | 2,4-Dichlorophenyl | |
| 192 | C(CH$_3$)(C$_3$H$_7$) | CHOH | 3,4-Dichlorophenyl | |
| 193 | C(CH$_3$)(C$_3$H$_7$) | CHOH | 2-Chloro-4-fluorophenyl | |
| 194 | C(CH$_3$)(C$_3$H$_7$) | CHOH | 2-Trifluoromethylphenyl | |
| 195 | C(CH$_3$)(C$_3$H$_7$) | CHOH | 4-Trifluoromethylphenyl | |
| 196 | C(CH$_3$)(C$_3$H$_7$) | CHOH | 4-Methoxyphenyl | |
| 197 | C(CH$_3$)(C$_3$H$_7$) | CHOH | 3,4-Dimethoxyphenyl | |
| 198 | C(CH$_3$)(C$_3$H$_7$) | CHOH | 4-Tetrafluoroethoxyphenyl | |
| 199 | C(CH$_3$)(C$_3$H$_7$) | CHOH | 4-Trifluoromethoxyphenyl | |
| 200 | C(CH$_3$)(C$_3$H$_7$) | CHOH | 2-Chloro-4-(4'-chlorophenoxy)phenyl | |
| 201 | C(CH$_3$)(C$_3$H$_7$) | CHOH | 4-Phenoxyphenyl | |
| 202 | C(CH$_3$)(C$_3$H$_7$) | CHOH | 4-(4'-Chlorophenoxy)phenyl | |
| 203 | C(CH$_3$)(C$_3$H$_7$) | CHOH | 4-Benzyloxyphenyl | |
| 204 | C(C$_2$H$_5$)(n-C$_4$H$_9$) | CHOH | Phenyl | oil 3196, 2956, 2934, 2869, 1452, 1424 |
| 205 | C(C$_2$H$_5$)(n-C$_4$H$_9$) | CHOH | 2-Methylphenyl | |
| 206 | C(C$_2$H$_5$)(n-C$_4$H$_9$) | CHOH | 4-Methylphenyl | oil 3200, 2956, 2933, 2870, 1478, 1457 |
| 207 | C(C$_2$H$_5$)(n-C$_4$H$_9$) | CHOH | 2,4-Dimethylphenyl | |
| 208 | C(C$_2$H$_5$)(n-C$_4$H$_9$) | CHOH | 2,6-Dimethylphenyl | |
| 209 | C(C$_2$H$_5$)(n-C$_4$H$_9$) | CHOH | 2,4,6-Trimethylphenyl | |
| 210 | C(C$_2$H$_5$)(n-C$_4$H$_9$) | CHOH | 4-tert. Butylphenyl | |
| 211 | C(C$_2$H$_5$)(n-C$_4$H$_9$) | CHOH | 1-Naphthyl | |
| 212 | C(C$_2$H$_5$)(n-C$_4$H$_9$) | CHOH | 2-Naphthyl | |
| 213 | C(C$_2$H$_5$)(n-C$_4$H$_9$) | CHOH | 4-Biphenyl | |
| 214 | C(C$_2$H$_5$)(n-C$_4$H$_9$) | CHOH | 2-Fluorophenyl | |
| 215 | C(C$_2$H$_5$)(n-C$_4$H$_9$) | CHOH | 4-Fluorophenyl | oil 3198, 2957, 2935, 2870, 1603, 1507 |
| 216 | C(C$_2$H$_5$)(n-C$_4$H$_9$) | CHOH | 2,4-Difluorophenyl | |
| 217 | C(C$_2$H$_5$)(n-C$_4$H$_9$) | CHOH | 2-Chlorophenyl | |
| 218 | C(C$_2$H$_5$)(n-C$_4$H$_9$) | CHOH | 3-Chlorophenyl | |
| 219 | C(C$_2$H$_5$)(n-C$_4$H$_9$) | CHOH | 4-Chlorophenyl | oil 2957, 2934, 2870, 1487, 1458, 1424 |
| 220 | C(C$_2$H$_5$)(n-C$_4$H$_9$) | CHOH | 2,4-Dichlorophenyl | |
| 221 | C(C$_2$H$_5$)(n-C$_4$H$_9$) | CHOH | 3,4-Dichlorophenyl | |
| 222 | C(C$_2$H$_5$)(n-C$_4$H$_9$) | CHOH | 2-Chloro-4-fluorophenyl | |
| 223 | C(C$_2$H$_5$)(n-C$_4$H$_9$) | CHOH | 2-Trifluoromethylphenyl | |
| 224 | C(C$_2$H$_5$)(n-C$_4$H$_9$) | CHOH | 4-Trifluoromethylphenyl | |
| 225 | C(C$_2$H$_5$)(n-C$_4$H$_9$) | CHOH | 4-Methoxyphenyl | |
| 226 | C(C$_2$H$_5$)(n-C$_4$H$_9$) | CHOH | 3,4-Dimethoxyphenyl | |
| 227 | C(C$_2$H$_5$)(n-C$_4$H$_9$) | CHOH | 4-Tetrafluoroethoxyphenyl | |
| 228 | C(C$_2$H$_5$)(n-C$_4$H$_9$) | CHOH | 4-Trifluoromethoxyphenyl | |
| 229 | C(C$_2$H$_5$)(n-C$_4$H$_9$) | CHOH | 2-Chloro-4-(4'-chlorophenoxy)-phenyl | |
| 230 | C(C$_2$H$_5$)(n-C$_4$H$_9$) | CHOH | 4-Phenoxyphenyl | |
| 231 | C(C$_2$H$_5$)(n-C$_4$H$_9$) | CHOH | 4-(4'-Chlorophenoxy)phenyl | |
| 232 | C(C$_2$H$_5$)(n-C$_4$H$_9$) | CHOH | 4-Benzyloxyphenyl | |
| 233 | CH(tert.C$_4$H$_9$) | CHOH | Phenyl | |
| 234 | CH(tert.C$_4$H$_9$) | CHOH | 2-Methylphenyl | |
| 235 | CH(tert.C$_4$H$_9$) | CHOH | 4-Methylphenyl | |
| 236 | CH(tert.C$_4$H$_9$) | CHOH | 2,4-Dimethylphenyl | |
| 237 | CH(tert.C$_4$H$_9$) | CHOH | 2,6-Dimethylphenyl | |
| 238 | CH(tert.C$_4$H$_9$) | CHOH | 2,4,6-Trimethylphenyl | |

TABLE-continued

| No. | A | B | Ar | Phys. data IR, cm$^{-1}$ |
|---|---|---|---|---|
| 239 | CH(tert.C$_4$H$_9$) | CHOH | 4-tert. Butylphenyl | |
| 240 | CH(tert.C$_4$H$_9$) | CHOH | 1-Naphthyl | |
| 241 | CH(tert.C$_4$H$_9$) | CHOH | 2-Naphthyl | |
| 242 | CH(tert.C$_4$H$_9$) | CHOH | 4-Biphenyl | |
| 243 | CH(tert.C$_4$H$_9$) | CHOH | 2-Fluorophenyl | |
| 244 | CH(tert.C$_4$H$_9$) | CHOH | 4-Fluorophenyl | oil 2.90, 2.75 (dd, 2H, —CH$_2$-Py) |
| 245 | CH(tert.C$_4$H$_9$) | CHOH | 2,4-Difluorophenyl | |
| 246 | CH(tert.C$_4$H$_9$) | CHOH | 2-Chlorophenyl | |
| 247 | CH(tert.C$_4$H$_9$) | CHOH | 3-Chlorophenyl | |
| 248 | CH(tert.C$_4$H$_9$) | CHOH | 4-Chlorophenyl | |
| 249 | CH(tert.C$_4$H$_9$) | CHOH | 2,4-Dichlorophenyl | |
| 250 | CH(tert.C$_4$H$_9$) | CHOH | 3,4-Dichlorophenyl | |
| 251 | CH(tert.C$_4$H$_9$) | CHOH | 2-Chloro-4-fluorophenyl | |
| 252 | CH(tert.C$_4$H$_9$) | CHOH | 2-Trifluoromethylphenyl | |
| 253 | CH(tert.C$_4$H$_9$) | CHOH | 4-Trifluoromethylphenyl | |
| 254 | CH(tert.C$_4$H$_9$) | CHOH | 4-Methoxyphenyl | |
| 255 | CH(tert.C$_4$H$_9$) | CHOH | 3,4-Dimethoxyphenyl | |
| 256 | CH(tert.C$_4$H$_9$) | CHOH | 4-Tetrafluoroethoxyphenyl | |
| 257 | CH(tert.C$_4$H$_9$) | CHOH | 4-Trifluoromethoxyphenyl | |
| 258 | CH(tert.C$_4$H$_9$) | CHOH | 2-Chloro-4-(4'-chlorophenoxy)phenyl | |
| 259 | CH(tert.C$_4$H$_9$) | CHOH | 4-Phenoxyphenyl | |
| 260 | CH(tert.C$_4$H$_9$) | CHOH | 4-(4'-Chlorophenoxy)phenyl | |
| 261 | CH(tert.C$_4$H$_9$) | CHOH | 4-Benzyloxyphenyl | |
| 262 | C(CH$_3$)$_2$ | C=O | Phenyl | |
| 263 | C(CH$_3$)$_2$ | C=O | 2-Methylphenyl | |
| 264 | C(CH$_3$)$_2$ | C=O | 4-Methylphenyl | oil 3.05 (s, 2H, —CH$_2$-Py) |
| 265 | C(CH$_3$)$_2$ | C=O | 2,4-Dimethylphenyl | |
| 266 | C(CH$_3$)$_2$ | C=O | 2,6-Dimethylphenyl | |
| 267 | C(CH$_3$)$_2$ | C=O | 2,4,6-Trimethylphenyl | |
| 268 | C(CH$_3$)$_2$ | C=O | 4-tert. Butylphenyl | |
| 269 | C(CH$_3$)$_2$ | C=O | 1-Naphthyl | |
| 270 | C(CH$_3$)$_2$ | C=O | 2-Naphthyl | |
| 271 | C(CH$_3$)$_2$ | C=O | 4-Biphenyl | |
| 272 | C(CH$_3$)$_2$ | C=O | 2-Fluorophenyl | |
| 273 | C(CH$_3$)$_2$ | C=O | 4-Fluorophenyl | oil 2932, 1670, 1588, 1479, 1453, 1423 |
| 274 | C(CH$_3$)$_2$ | C=O | 2,4-Difluorophenyl | |
| 275 | C(CH$_3$)$_2$ | C=O | 2-Chlorophenyl | |
| 276 | C(CH$_3$)$_2$ | C=O | 3-Chlorophenyl | |
| 277 | C(CH$_3$)$_2$ | C=O | 4-Chlorophenyl | oil 3.05 (s, 2H, —CH$_2$-Py) |
| 278 | C(CH$_3$)$_2$ | C=O | 2,4-Dichlorophenyl | |
| 279 | C(CH$_3$)$_2$ | C=O | 3,4-Dichlorophenyl | |
| 280 | C(CH$_3$)$_2$ | C=O | 2-Chloro-4-fluorophenyl | |
| 281 | C(CH$_3$)$_2$ | C=O | 2-Trifluoromethylphenyl | |
| 282 | C(CH$_3$)$_2$ | C=O | 4-Trifluoromethylphenyl | |
| 283 | C(CH$_3$)$_2$ | C=O | 4-Methoxyphenyl | |
| 284 | C(CH$_3$)$_2$ | C=O | 3,4-Dimethoxyphenyl | |
| 285 | C(CH$_3$)$_2$ | C=O | 4-Tetrafluoroethoxyphenyl | |
| 286 | C(CH$_3$)$_2$ | C=O | 4-Trifluoromethoxyphenyl | |
| 287 | C(CH$_3$)$_2$ | C=O | 2-Chloro-4-(4'-chlorophenoxy)phenyl | |
| 288 | C(CH$_3$)$_2$ | C=O | 4-Phenoxyphenyl | |
| 289 | C(CH$_3$)$_2$ | C=O | 4-(4'-Chlorophenoxy)phenyl | |
| 290 | C(CH$_3$)$_2$ | C=O | 4-Benzyloxyphenyl | |
| 291 | C(CH$_3$)(CH$_2$CH$_3$) | C=O | Phenyl | |
| 292 | C(CH$_3$)(CH$_2$CH$_3$) | C=O | 2-Methylphenyl | |
| 293 | C(CH$_3$)(CH$_2$CH$_3$) | C=O | 4-Methylphenyl | |
| 294 | C(CH$_3$)(CH$_2$CH$_3$) | C=O | 2,4-Dimethylphenyl | |
| 295 | C(CH$_3$)(CH$_2$CH$_3$) | C=O | 2,6-Dimethylphenyl | |
| 296 | C(CH$_3$)(CH$_2$CH$_3$) | C=O | 2,4,6-Trimethylphenyl | |
| 297 | C(CH$_3$)(CH$_2$CH$_3$) | C=O | 4-tert. Butylphenyl | |
| 298 | C(CH$_3$)(CH$_2$CH$_3$) | C=O | 1-Naphthyl | |
| 299 | C(CH$_3$)(CH$_2$CH$_3$) | C=O | 2-Naphthyl | |
| 300 | C(CH$_3$)(CH$_2$CH$_3$) | C=O | 4-Biphenyl | |
| 301 | C(CH$_3$)(CH$_2$CH$_3$) | C=O | 2-Fluorophenyl | |
| 302 | C(CH$_3$)(CH$_2$CH$_3$) | C=O | 4-Fluorophenyl | |
| 303 | C(CH$_3$)(CH$_2$CH$_3$) | C=O | 2,4-Difluorophenyl | |
| 304 | C(CH$_3$)(CH$_2$CH$_3$) | C=O | 2-Chlorophenyl | |
| 305 | C(CH$_3$)(CH$_2$CH$_3$) | C=O | 3-Chlorophenyl | |
| 306 | C(CH$_3$)(CH$_2$CH$_3$) | C=O | 4-Chlorophenyl | |
| 307 | C(CH$_3$)(CH$_2$CH$_3$) | C=O | 2,4-Dichlorophenyl | |
| 308 | C(CH$_3$)(CH$_2$CH$_3$) | C=O | 3,4-Dichlorophenyl | |
| 309 | C(CH$_3$)(CH$_2$CH$_3$) | C=O | 2-Chloro-4-fluorophenyl | |
| 310 | C(CH$_3$)(CH$_2$CH$_3$) | C=O | 2-Trifluoromethylphenyl | |
| 311 | C(CH$_3$)(CH$_2$CH$_3$) | C=O | 4-Trifluoromethylphenyl | |
| 312 | C(CH$_3$)(CH$_2$CH$_3$) | C=O | 4-Methoxyphenyl | |
| 313 | C(CH$_3$)(CH$_2$CH$_3$) | C=O | 3,4-Dimethoxyphenyl | |
| 314 | C(CH$_3$)(CH$_2$CH$_3$) | C=O | 4-Tetrafluoroethoxyphenyl | |
| 315 | C(CH$_3$)(CH$_2$CH$_3$) | C=O | 4-Trifluoromethoxyphenyl | |
| 316 | C(CH$_3$)(CH$_2$CH$_3$) | C=O | 2-Chloro-4-(4'-chlorophenoxy)phenyl | |
| 317 | C(CH$_3$)(CH$_2$CH$_3$) | C=O | 4-Phenoxyphenyl | |
| 318 | C(CH$_3$)(CH$_2$CH$_3$) | C=O | 4-(4'-Chlorophenoxy)phenyl | |
| 319 | C(CH$_3$)(CH$_2$CH$_3$) | C=O | 4-Benzyloxyphenyl | |

TABLE-continued

| No. | A | B | Ar | Phys. data IR, cm$^{-1}$ |
|---|---|---|---|---|
| 320 | C(CH$_2$CH$_3$)$_2$ | C=O | Phenyl | |
| 321 | C(CH$_2$CH$_3$)$_2$ | C=O | 2-Methylphenyl | |
| 322 | C(CH$_2$CH$_3$)$_2$ | C=O | 4-Methylphenyl | |
| 323 | C(CH$_2$CH$_3$)$_2$ | C=O | 2,4-Dimethylphenyl | |
| 324 | C(CH$_2$CH$_3$)$_2$ | C=O | 2,6-Dimethylphenyl | |
| 325 | C(CH$_2$CH$_3$)$_2$ | C=O | 2,4,6-Trimethylphenyl | |
| 326 | C(CH$_2$CH$_3$)$_2$ | C=O | 4-tert. Butylphenyl | |
| 327 | C(CH$_2$CH$_3$)$_2$ | C=O | 1-Naphthyl | |
| 328 | C(CH$_2$CH$_3$)$_2$ | C=O | 2-Naphthyl | |
| 329 | C(CH$_2$CH$_3$)$_2$ | C=O | 4-Biphenyl | |
| 330 | C(CH$_2$CH$_3$)$_2$ | C=O | 2-Fluorophenyl | |
| 331 | C(CH$_2$CH$_3$)$_2$ | C=O | 4-Fluorophenyl | oil 3.08 (s, 2H, —CH$_2$-Py) |
| 332 | C(CH$_2$CH$_3$)$_2$ | C=O | 2,4-Difluorophenyl | |
| 333 | C(CH$_2$CH$_3$)$_2$ | C=O | 2-Chlorophenyl | |
| 334 | C(CH$_2$CH$_3$)$_2$ | C=O | 3-Chlorophenyl | |
| 335 | C(CH$_2$CH$_3$)$_2$ | C=O | 4-Chlorophenyl | |
| 336 | C(CH$_2$CH$_3$)$_2$ | C=O | 2,4-Dichlorophenyl | |
| 337 | C(CH$_2$CH$_3$)$_2$ | C=O | 3,4-Dichlorophenyl | |
| 338 | C(CH$_2$CH$_3$)$_2$ | C=O | 2-Chloro-4-fluorophenyl | |
| 339 | C(CH$_2$CH$_3$)$_2$ | C=O | 2-Trifluoromethylphenyl | |
| 340 | C(CH$_2$CH$_3$)$_2$ | C=O | 4-Trifluoromethylphenyl | |
| 341 | C(CH$_2$CH$_3$)$_2$ | C=O | 4-Methoxyphenyl | |
| 342 | C(CH$_2$CH$_3$)$_2$ | C=O | 3,4-Dimethoxyphenyl | |
| 343 | C(CH$_2$CH$_3$)$_2$ | C=O | 4-Tetrafluoroethoxyphenyl | |
| 344 | C(CH$_2$CH$_3$)$_2$ | C=O | 4-Trifluoromethoxyphenyl | |
| 345 | C(CH$_2$CH$_3$)$_2$ | C=O | 2-Chloro-4-(4'-chlorophenoxy)phenyl | |
| 346 | C(CH$_2$CH$_3$)$_2$ | C=O | 4-Phenoxyphenyl | |
| 347 | C(CH$_2$CH$_3$)$_2$ | C=O | 4-(4'-Chlorophenoxy)phenyl | |
| 348 | C(CH$_2$CH$_3$)$_2$ | C=O | 4-Benzyloxyphenyl | |
| 349 | Cyclopropylene | C=O | Phenyl | |
| 350 | Cyclopropylene | C=O | 2-Methylphenyl | |
| 351 | Cyclopropylene | C=O | 4-Methylphenyl | oil 1671, 1808, 1423, 1177, 831, 715 |
| 352 | Cyclopropylene | C=O | 2,4-Dimethylphenyl | |
| 353 | Cyclopropylene | C=O | 2,6-Dimethylphenyl | |
| 354 | Cyclopropylene | C=O | 2,4,6-Trimethylphenyl | |
| 355 | Cyclopropylene | C=O | 4-tert. Butylphenyl | |
| 356 | Cyclopropylene | C=O | 1-Naphthyl | |
| 357 | Cyclopropylene | C=O | 2-Naphthyl | |
| 358 | Cyclopropylene | C=O | 4-Biphenyl | |
| 359 | Cyclopropylene | C=O | 2-Fluorophenyl | |
| 360 | Cyclopropylene | C=O | 4-Fluorophenyl | oil 1676, 1600, 1505, 1229, 848, 715 |
| 361 | Cyclopropylene | C=O | 2,4-Difluorophenyl | |
| 362 | Cyclopropylene | C=O | 2-Chlorophenyl | |
| 363 | Cyclopropylene | C=O | 3-Chlorophenyl | |
| 364 | Cyclopropylene | C=O | 4-Chlorophenyl | oil 1675, 1589, 1424, 1051, 841, 715 |
| 365 | Cyclopropylene | C=O | 2,4-Dichlorophenyl | |
| 366 | Cyclopropylene | C=O | 3,4-Dichlorophenyl | |
| 367 | Cyclopropylene | C=O | 2-Chloro-4-fluorophenyl | |
| 368 | Cyclopropylene | C=O | 2-Trifluoromethylphenyl | |
| 369 | Cyclopropylene | C=O | 4-Trifluoromethylphenyl | |
| 370 | Cyclopropylene | C=O | 4-Methoxyphenyl | |
| 371 | Cyclopropylene | C=O | 3,4-Dimethyloxyphenyl | |
| 372 | Cyclopropylene | C=O | 4-Tetrafluoroethoxyphenyl | |
| 373 | Cyclopropylene | C=O | 4-Trifluoromethoxyphenyl | |
| 374 | Cyclopropylene | C=O | 2-Chloro-4-(4'-chlorophenoxy)phenyl | |
| 375 | Cyclopropylene | C=O | 4-Phenoxyphenyl | |
| 376 | Cyclopropylene | C=O | 4-(4'-Chlorophenoxy)phenyl | |
| 377 | Cyclopropylene | C=O | 4-Benzyloxyphenyl | |
| 378 | Cyclopentylene | C=O | Phenyl | |
| 379 | Cyclopentylene | C=O | 2-Methylphenyl | |
| 380 | Cyclopentylene | C=O | 4-Methylphenyl | |
| 381 | Cyclopentylene | C=O | 2,4-Dimethylphenyl | |
| 382 | Cyclopentylene | C=O | 2,6-Dimethylphenyl | |
| 383 | Cyclopentylene | C=O | 2,4,6-Trimethylphenyl | |
| 384 | Cyclopentylene | C=O | 4-tert. Butylphenyl | |
| 385 | Cyclopentylene | C=O | 1-Naphthyl | |
| 386 | Cyclopentylene | C=O | 2-Naphthyl | |
| 387 | Cyclopentylene | C=O | 4-Biphenyl | |
| 388 | Cyclopentylene | C=O | 2-Fluorophenyl | |
| 389 | Cyclopentylene | C=O | 4-Fluorophenyl | oil 3.15 (s, 2H, —CH$_2$-Py) |
| 390 | Cyclopentylene | C=O | 2,4-Difluorophenyl | |
| 391 | Cyclopentylene | C=O | 2-Chlorophenyl | |
| 392 | Cyclopentylene | C=O | 3-Chlorophenyl | |
| 393 | Cyclopentylene | C=O | 4-Chlorophenyl | oil 3.15 (s, 2H, —CH$_2$-Py) |
| 394 | Cyclopentylene | C=O | 2,4-Dichlorophenyl | oil 1691, 1583, 1423, 1105, 825, 717 |
| 395 | Cyclopentylene | C=O | 3,4-Dichlorophenyl | |
| 396 | Cyclopentylene | C=O | 2-Chloro-4-fluorophenyl | |
| 397 | Cyclopentylene | C=O | 2-Trifluoromethylphenyl | |
| 398 | Cyclopentylene | C=O | 4-Trifluoromethylphenyl | |
| 399 | Cyclopentylene | C=O | 4-Methoxyphenyl | |
| 400 | Cyclopentylene | C=O | 3,4-Dimethoxyphenyl | |

TABLE-continued

| No. | A | B | Ar | Phys. data IR. cm$^{-1}$ |
|---|---|---|---|---|
| 401 | Cyclopentylene | C=O | 4-Tetrafluoroethoxyphenyl | |
| 402 | Cyclopentylene | C=O | 4-Trifluoromethoxyphenyl | |
| 403 | Cyclopentylene | C=O | 2-Chloro-4-(4'-chlorophenoxy)phenyl | |
| 404 | Cyclopentylene | C=O | 4-Phenoxyphenyl | |
| 405 | Cyclopentylene | C=O | 4-(4'-Chlorophenoxy)phenyl | |
| 406 | Cyclopentylene | C=O | 4-Benzyloxyphenyl | |
| 407 | Cyclohexylene | C=O | Phenyl | |
| 408 | Cyclohexylene | C=O | 2-Methylphenyl | |
| 409 | Cyclohexylene | C=O | 4-Methylphenyl | |
| 410 | Cyclohexylene | C=O | 2,4-Dimethylphenyl | |
| 411 | Cyclohexylene | C=O | 2,6-Dimethylphenyl | |
| 412 | Cyclohexylene | C=O | 2,4,6-Trimethylphenyl | |
| 413 | Cyclohexylene | C=O | 4-tert. Butylphenyl | |
| 414 | Cyclohexylene | C=O | 1-Naphthyl | |
| 415 | Cyclohexylene | C=O | 2-Naphthyl | |
| 416 | Cyclohexylene | C=O | 4-Biphenyl | |
| 417 | Cyclohexylene | C=O | 2-Fluorophenyl | |
| 418 | Cyclohexylene | C=O | 4-Fluorophenyl | |
| 419 | Cyclohexylene | C=O | 2,4-Difluorophenyl | |
| 420 | Cyclohexylene | C=O | 2-Chlorophenyl | |
| 421 | Cyclohexylene | C=O | 3-Chlorophenyl | |
| 422 | Cyclohexylene | C=O | 4-Chlorophenyl | oil 3.1 (s, 2H, —CH$_2$-Py) |
| 423 | Cyclohexylene | C=O | 2,4-Dichlorophenyl | |
| 424 | Cyclohexylene | C=O | 3,4-Dichlorophenyl | |
| 425 | Cyclohexylene | C=O | 2-Chloro-4-fluorophenyl | |
| 426 | Cyclohexylene | C=O | 2-Trifluoromethylphenyl | |
| 427 | Cyclohexylene | C=O | 4-Trifluoromethylphenyl | |
| 428 | Cyclohexylene | C=O | 4-Methoxyphenyl | |
| 429 | Cyclohexylene | C=O | 3,4-Dimethoxyphenyl | |
| 430 | Cyclohexylene | C=O | 4-Tetrafluoroethoxyphenyl | |
| 431 | Cyclohexylene | C=O | 4-Trifluoromethoxyphenyl | |
| 432 | Cyclohexylene | C=O | 2-Chloro-4-(4'-chlorophenoxy)phenyl | |
| 433 | Cyclohexylene | C=O | 4-Phenoxyphenyl | |
| 434 | Cyclohexylene | C=O | 4-(4'-Chlorophenoxy)phenyl | |
| 435 | Cyclohexylene | C=O | 4-Benzyloxyphenyl | |
| 436 | C(CH$_3$)(C$_3$H$_7$) | C=O | Phenyl | |
| 437 | C(CH$_3$)(C$_3$H$_7$) | C=O | 2-Methylphenyl | |
| 438 | C(CH$_3$)(C$_3$H$_7$) | C=O | 4-Methylphenyl | |
| 439 | C(CH$_3$)(C$_3$H$_7$) | C=O | 2,4-Dimethylphenyl | |
| 440 | C(CH$_3$)(C$_3$H$_7$) | C=O | 2,6-Dimethylphenyl | |
| 441 | C(CH$_3$)(C$_3$H$_7$) | C=O | 2,4,6-Trimethylphenyl | |
| 442 | C(CH$_3$)(C$_3$H$_7$) | C=O | 4-tert. Butylphenyl | |
| 443 | C(CH$_3$)(C$_3$H$_7$) | C=O | 1-Naphthyl | |
| 444 | C(CH$_3$)(C$_3$H$_7$) | C=O | 2-Naphthyl | |
| 445 | C(CH$_3$)(C$_3$H$_7$) | C=O | 4-Biphenyl | |
| 446 | C(CH$_3$)(C$_3$H$_7$) | C=O | 2-Fluorophenyl | |
| 447 | C(CH$_3$)(C$_3$H$_7$) | C=O | 4-Fluorophenyl | |
| 448 | C(CH$_3$)(C$_3$H$_7$) | C=O | 2,4-Difluorophenyl | |
| 449 | C(CH$_3$)(C$_3$H$_7$) | C=O | 2-Chlorophenyl | |
| 450 | C(CH$_3$)(C$_3$H$_7$) | C=O | 3-Chlorophenyl | |
| 451 | C(CH$_3$)(C$_3$H$_7$) | C=O | 4-Chlorophenyl | |
| 452 | C(CH$_3$)(C$_3$H$_7$) | C=O | 2,4-Dichlorophenyl | |
| 453 | C(CH$_3$)(C$_3$H$_7$) | C=O | 3,4-Dichlorophenyl | |
| 454 | C(CH$_3$)(C$_3$H$_7$) | C=O | 2-Chloro-4-fluorophenyl | |
| 455 | C(CH$_3$)(C$_3$H$_7$) | C=O | 2-Trifluoromethylphenyl | |
| 456 | C(CH$_3$)(C$_3$H$_7$) | C=O | 4-Trifluoromethylphenyl | |
| 457 | C(CH$_3$)(C$_3$H$_7$) | C=O | 4-Methoxyphenyl | |
| 458 | C(CH$_3$)(C$_3$H$_7$) | C=O | 3,4-Dimethoxyphenyl | |
| 459 | C(CH$_3$)(C$_3$H$_7$) | C=O | 4-Tetrafluoroethoxyphenyl | |
| 460 | C(CH$_3$)(C$_3$H$_7$) | C=O | 4-Trifluoromethoxyphenyl | |
| 461 | C(CH$_3$)(C$_3$H$_7$) | C=O | 2-Chloro-4-(4'-chlorophenoxy)phenyl | |
| 462 | C(CH$_3$)(C$_3$H$_7$) | C=O | 4-Phenoxyphenyl | |
| 463 | C(CH$_3$)(C$_3$H$_7$) | C=O | 4-(4'-Chlorophenoxy)phenyl | |
| 464 | C(CH$_3$)(C$_3$H$_7$) | C=O | 4-Benzyloxyphenyl | |
| 465 | C(CH$_2$H$_5$)(n-C$_4$H$_9$) | C=O | Phenyl | |
| 466 | C(CH$_2$H$_5$)(n-C$_4$H$_9$) | C=O | 2-Methylphenyl | |
| 467 | C(CH$_2$H$_5$)(n-C$_4$H$_9$) | C=O | 4-Methylphenyl | |
| 468 | C(CH$_2$H$_5$)(n-C$_4$H$_9$) | C=O | 2,4-Dimethylphenyl | |
| 469 | C(CH$_2$H$_5$)(n-C$_4$H$_9$) | C=O | 2,6-Dimethylphenyl | |
| 470 | C(CH$_2$H$_5$)(n-C$_4$H$_9$) | C=O | 2,4,6-Trimethylphenyl | |
| 471 | C(CH$_2$H$_5$)(n-C$_4$H$_9$) | C=O | 4-tert. Butylphenyl | |
| 472 | C(CH$_2$H$_5$)(n-C$_4$H$_9$) | C=O | 1-Naphthyl | |
| 473 | C(CH$_2$H$_5$)(n-C$_4$H$_9$) | C=O | 2-Naphthyl | |
| 474 | C(CH$_2$H$_5$)(n-C$_4$H$_9$) | C=O | 4-Biphenyl | |
| 475 | C(CH$_2$H$_5$)(n-C$_4$H$_9$) | C=O | 2-Fluorophenyl | |
| 476 | C(CH$_2$H$_5$)(n-C$_4$H$_9$) | C=O | 4-Fluorophenyl | |
| 477 | C(CH$_2$H$_5$)(n-C$_4$H$_9$) | C=O | 2,4-Difluorophenyl | |
| 478 | C(CH$_2$H$_5$)(n-C$_4$H$_9$) | C=O | 2-Chlorophenyl | |
| 479 | C(CH$_2$H$_5$)(n-C$_4$H$_9$) | C=O | 3-Chlorophenyl | |
| 480 | C(CH$_2$H$_5$)(n-C$_4$H$_9$) | C=O | 4-Chlorophenyl | |
| 481 | C(CH$_2$H$_5$)(n-C$_4$H$_9$) | C=O | 2,4-Dichlorophenyl | |

TABLE-continued

| No. | A | B | Ar | Phys. data IR, cm$^{-1}$ |
|---|---|---|---|---|
| 482 | C(CH$_2$H$_5$)(n-C$_4$H$_9$) | C=O | 3,4-Dichlorophenyl | |
| 483 | C(CH$_2$H$_5$)(n-C$_4$H$_9$) | C=O | 2-Chloro-4-fluorophenyl | |
| 484 | C(CH$_2$H$_5$)(n-C$_4$H$_9$) | C=O | 2-Trifluoromethylphenyl | |
| 485 | C(CH$_2$H$_5$)(n-C$_4$H$_9$) | C=O | 4-Trifluoromethylphenyl | |
| 486 | C(CH$_2$H$_5$)(n-C$_4$H$_9$) | C=O | 4-Methoxyphenyl | |
| 487 | C(CH$_2$H$_5$)(n-C$_4$H$_9$) | C=O | 3,4-Dimethoxyphenyl | |
| 488 | C(CH$_2$H$_5$)(n-C$_4$H$_9$) | C=O | 4-Tetrafluoroethoxyphenyl | |
| 489 | C(CH$_2$H$_5$)(n-C$_4$H$_9$) | C=O | 4-Trifluoromethoxyphenyl | |
| 490 | C(CH$_2$H$_5$)(n-C$_4$H$_9$) | C=O | 2-Chloro-4-(4'-chlorophenoxy)-phenyl | |
| 491 | C(CH$_2$H$_5$)(n-C$_4$H$_9$) | C=O | 4-Phenoxyphenyl | |
| 492 | C(CH$_2$H$_5$)(n-C$_4$H$_9$) | C=O | 4-(4'-Chlorophenoxy)phenyl | |
| 493 | C(CH$_2$H$_5$)(n-C$_4$H$_9$) | C=O | 4-Benzyloxyphenyl | |
| 494 | CH(tert.C$_4$H$_9$) | C=O | Phenyl | |
| 495 | CH(tert.C$_4$H$_9$) | C=O | 2-Methylphenyl | |
| 496 | CH(tert.C$_4$H$_9$) | C=O | 4-Methylphenyl | |
| 497 | CH(tert.C$_4$H$_9$) | C=O | 2,4-Dimethylphenyl | |
| 498 | CH(tert.C$_4$H$_9$) | C=O | 2,6-Dimethylphenyl | |
| 499 | CH(tert.C$_4$H$_9$) | C=O | 2,4,6-Trimethylphenyl | |
| 500 | CH(tert.C$_4$H$_9$) | C=O | 4-tert. Butylphenyl | |
| 501 | CH(tert.C$_4$H$_9$) | C=O | 1-Naphthyl | |
| 502 | CH(tert.C$_4$H$_9$) | C=O | 2-Naphthyl | |
| 503 | CH(tert.C$_4$H$_9$) | C=O | 4-Biphenyl | |
| 504 | CH(tert.C$_4$H$_9$) | C=O | 2-Fluorophenyl | |
| 505 | CH(tert.C$_4$H$_9$) | C=O | 4-Fluorophenyl | |
| 506 | CH(tert.C$_4$H$_9$) | C=O | 2,4-Difluorophenyl | |
| 507 | CH(tert.C$_4$H$_9$) | C=O | 2-Chlorophenyl | |
| 508 | CH(tert.C$_4$H$_9$) | C=O | 3-Chlorophenyl | |
| 509 | CH(tert.C$_4$H$_9$) | C=O | 4-Chlorophenyl | |
| 510 | CH(tert.C$_4$H$_9$) | C=O | 2,4-Dichlorophenyl | |
| 511 | CH(tert.C$_4$H$_9$) | C=O | 3,4-Dichlorophenyl | |
| 512 | CH(tert.C$_4$H$_9$) | C=O | 2-Chloro-4-fluorophenyl | |
| 513 | CH(tert.C$_4$H$_9$) | C=O | 2-Trifluoromethylphenyl | |
| 514 | CH(tert.C$_4$H$_9$) | C=O | 4-Trifluoromethylphenyl | |
| 515 | CH(tert.C$_4$H$_9$) | C=O | 4-Methoxyphenyl | |
| 516 | CH(tert.C$_4$H$_9$) | C=O | 3,4-Dimethoxyphenyl | |
| 517 | CH(tert.C$_4$H$_9$) | C=O | 4-Tetrafluoroethoxyphenyl | |
| 518 | CH(tert.C$_4$H$_9$) | C=O | 4-Trifluoromethoxyphenyl | |
| 519 | CH(tert.C$_4$H$_9$) | C=O | 2-Chloro-4-(4'-chlorophenoxy)phenyl | |
| 520 | CH(tert.C$_4$H$_9$) | C=O | 4-Phenoxyphenyl | |
| 521 | CH(tert.C$_4$H$_9$) | C=O | 4-(4'-Chlorophenoxy)phenyl | |
| 522 | CH(tert.C$_4$H$_9$) | C=O | 4-Benzyloxyphenyl | |
| 523 | C(CH$_3$)$_2$ | CHCl | Phenyl | 75–80° C. |
| 524 | C(CH$_3$)$_2$ | CHCl | 2-Methylphenyl | 212–215° C. |
| 525 | C(CH$_3$)$_2$ | CHCl | 4-Methylphenyl | 108–109° C. |
| 526 | C(CH$_3$)$_2$ | CHCl | 2,4-Dimethylphenyl | |
| 527 | C(CH$_3$)$_2$ | CHCl | 2,6-Dimethylphenyl | |
| 528 | C(CH$_3$)$_2$ | CHCl | 2,4,6-Trimethylphenyl | 215–218° C. |
| 529 | C(CH$_3$)$_2$ | CHCl | 4-tert. Butylphenyl | 143–147° C. |
| 530 | C(CH$_3$)$_2$ | CHCl | 1-Naphthyl | |
| 531 | C(CH$_3$)$_2$ | CHCl | 2-Naphthyl | |
| 532 | C(CH$_3$)$_2$ | CHCl | 4-Biphenyl | |
| 533 | C(CH$_3$)$_2$ | CHCl | 2-Fluorophenyl | |
| 534 | C(CH$_3$)$_2$ | CHCl | 4-Fluorophenyl | |
| 535 | C(CH$_3$)$_2$ | CHCl | 2,4-Difluorophenyl | |
| 536 | C(CH$_3$)$_2$ | CHCl | 2-Chlorophenyl | |
| 537 | C(CH$_3$)$_2$ | CHCl | 3-Chlorophenyl | |
| 538 | C(CH$_3$)$_2$ | CHCl | 4-Chlorophenyl | 155–158° C. |
| 539 | C(CH$_3$)$_2$ | CHCl | 2,4-Dichlorophenyl | |
| 540 | C(CH$_3$)$_2$ | CHCl | 3,4-Dichlorophenyl | |
| 541 | C(CH$_3$)$_2$ | CHCl | 2-Chloro-4-fluorophenyl | |
| 542 | C(CH$_3$)$_2$ | CHCl | 2-Trifluoromethylphenyl | |
| 543 | C(CH$_3$)$_2$ | CHCl | 4-Trifluoromethylphenyl | |
| 544 | C(CH$_3$)$_2$ | CHCl | 4-Methoxyphenyl | |
| 545 | C(CH$_3$)$_2$ | CHCl | 3,4-Dimethoxyphenyl | |
| 546 | C(CH$_3$)$_2$ | CHCl | 4-Tetrafluoroethoxyphenyl | |
| 547 | C(CH$_3$)$_2$ | CHCl | 4-Trifluoromethoxyphenyl | |
| 548 | C(CH$_3$)$_2$ | CHCl | 2-Chloro-4-(4'-chlorophenoxy)phenyl | |
| 549 | C(CH$_3$)$_2$ | CHCl | 4-Phenoxyphenyl | |
| 550 | C(CH$_3$)$_2$ | CHCl | 4-(4'-Chlorophenoxy)phenyl | |
| 551 | C(CH$_3$)$_2$ | CHCl | 4-Benzyloxyphenyl | |
| 552 | C(CH$_3$)(CH$_2$CH$_3$) | CHCl | Phenyl | |
| 553 | C(CH$_3$)(CH$_2$CH$_3$) | CHCl | 2-Methylphenyl | |
| 554 | C(CH$_3$)(CH$_2$CH$_3$) | CHCl | 4-Methylphenyl | |
| 555 | C(CH$_3$)(CH$_2$CH$_3$) | CHCl | 2,4-Dimethylphenyl | |
| 556 | C(CH$_3$)(CH$_2$CH$_3$) | CHCl | 2,6-Dimethylphenyl | |
| 557 | C(CH$_3$)(CH$_2$CH$_3$) | CHCl | 2,4,6-Trimethylphenyl | |
| 558 | C(CH$_3$)(CH$_2$CH$_3$) | CHCl | 4-tert. Butylphenyl | |
| 559 | C(CH$_3$)(CH$_2$CH$_3$) | CHCl | 1-Naphthyl | |
| 560 | C(CH$_3$)(CH$_2$CH$_3$) | CHCl | 2-Naphthyl | |
| 561 | C(CH$_3$)(CH$_2$CH$_3$) | CHCl | 4-Biphenyl | |
| 562 | C(CH$_3$)(CH$_2$CH$_3$) | CHCl | 2-Fluorophenyl | |

TABLE-continued

| No. | A | B | Ar | Phys. data IR, cm$^{-1}$ |
|---|---|---|---|---|
| 563 | C(CH$_3$)(CH$_2$CH$_3$) | CHCl | 4-Fluorophenyl | |
| 564 | C(CH$_3$)(CH$_2$CH$_3$) | CHCl | 2,4-Difluorophenyl | |
| 565 | C(CH$_3$)(CH$_2$CH$_3$) | CHCl | 2-Chlorophenyl | |
| 566 | C(CH$_3$)(CH$_2$CH$_3$) | CHCl | 3-Chlorophenyl | |
| 567 | C(CH$_3$)(CH$_2$CH$_3$) | CHCl | 4-Chlorophenyl | |
| 568 | C(CH$_3$)(CH$_2$CH$_3$) | CHCl | 2,4-Dichlorophenyl | |
| 569 | C(CH$_3$)(CH$_2$CH$_3$) | CHCl | 3,4-Dichlorophenyl | |
| 570 | C(CH$_3$)(CH$_2$CH$_3$) | CHCl | 2-Chloro-4-fluorophenyl | |
| 571 | C(CH$_3$)(CH$_2$CH$_3$) | CHCl | 2-Trifluoromethylphenyl | |
| 572 | C(CH$_3$)(CH$_2$CH$_3$) | CHCl | 4-Trifluoromethylphenyl | |
| 573 | C(CH$_3$)(CH$_2$CH$_3$) | CHCl | 4-Methoxyphenyl | |
| 574 | C(CH$_3$)(CH$_2$CH$_3$) | CHCl | 3,4-Dimethoxyphenyl | |
| 575 | C(CH$_3$)(CH$_2$CH$_3$) | CHCl | 4-Tetrafluoroethoxyphenyl | |
| 576 | C(CH$_3$)(CH$_2$CH$_3$) | CHCl | 4-Trifluoromethoxyphenyl | |
| 577 | C(CH$_3$)(CH$_2$CH$_3$) | CHCl | 2-Chloro-4-(4'-chlorophenoxy)phenyl | |
| 578 | C(CH$_3$)(CH$_2$CH$_3$) | CHCl | 4-Phenoxyphenyl | |
| 579 | C(CH$_3$)(CH$_2$CH$_3$) | CHCl | 4-(4'-Chlorophenoxy)phenyl | |
| 580 | C(CH$_3$)(CH$_2$CH$_3$) | CHCl | 4-Benzyloxyphenyl | |
| 581 | C(CH$_2$CH$_3$)$_2$ | CHCl | Phenyl | oil 2967, 2939, 1478, 1452, 1423, 1027 |
| 582 | C(CH$_2$CH$_3$)$_2$ | CHCl | 2-Methylphenyl | 153–155° C. |
| 583 | C(CH$_2$CH$_3$)$_2$ | CHCl | 4-Methylphenyl | |
| 584 | C(CH$_2$CH$_3$)$_2$ | CHCl | 2,4-Dimethylphenyl | |
| 585 | C(CH$_2$CH$_3$)$_2$ | CHCl | 2,6-Dimethylphenyl | |
| 586 | C(CH$_2$CH$_3$)$_2$ | CHCl | 2,4,6-Trimethylphenyl | 142–146° C. |
| 587 | C(CH$_2$CH$_3$)$_2$ | CHCl | 4-tert. Butylphenyl | |
| 588 | C(CH$_2$CH$_3$)$_2$ | CHCl | 1-Naphthyl | |
| 589 | C(CH$_2$CH$_3$)$_2$ | CHCl | 2-Naphthyl | |
| 590 | C(CH$_2$CH$_3$)$_2$ | CHCl | 4-Biphenyl | |
| 591 | C(CH$_2$CH$_3$)$_2$ | CHCl | 2-Fluorophenyl | |
| 592 | C(CH$_2$CH$_3$)$_2$ | CHCl | 4-Fluorophenyl | |
| 593 | C(CH$_2$CH$_3$)$_2$ | CHCl | 2,4-Difluorophenyl | |
| 594 | C(CH$_2$CH$_3$)$_2$ | CHCl | 2-Chlorophenyl | |
| 595 | C(CH$_2$CH$_3$)$_2$ | CHCl | 3-Chlorophenyl | |
| 596 | C(CH$_2$CH$_3$)$_2$ | CHCl | 4-Chlorophenyl | |
| 597 | C(CH$_2$CH$_3$)$_2$ | CHCl | 2,4-Dichlorophenyl | |
| 598 | C(CH$_2$CH$_3$)$_2$ | CHCl | 3,4-Dichlorophenyl | |
| 599 | C(CH$_2$CH$_3$)$_2$ | CHCl | 2-Chloro-4-fluorophenyl | |
| 600 | C(CH$_2$CH$_3$)$_2$ | CHCl | 2-Trifluoromethylphenyl | |
| 601 | C(CH$_2$CH$_3$)$_2$ | CHCl | 4-Trifluoromethylphenyl | |
| 602 | C(CH$_2$CH$_3$)$_2$ | CHCl | 4-Methoxyphenyl | 87° C. |
| 603 | C(CH$_2$CH$_3$)$_2$ | CHCl | 3,4-Dimethoxyphenyl | |
| 604 | C(CH$_2$CH$_3$)$_2$ | CHCl | 4-Tetrafluoroethoxyphenyl | |
| 605 | C(CH$_2$CH$_3$)$_2$ | CHCl | 4-Trifluoromethoxyphenyl | |
| 606 | C(CH$_2$CH$_3$)$_2$ | CHCl | 2-Chloro-4-(4'-chlorophenoxy)phenyl | |
| 607 | C(CH$_2$CH$_3$)$_2$ | CHCl | 4-Phenoxyphenyl | |
| 608 | C(CH$_2$CH$_3$)$_2$ | CHCl | 4-(4'-Chlorophenoxy)phenyl | |
| 609 | C(CH$_2$CH$_3$)$_2$ | CHCl | 4-Benzyloxyphenyl | |
| 610 | Cyclopropylene | CHCl | Phenyl | |
| 611 | Cyclopropylene | CHCl | 2-Methylphenyl | |
| 612 | Cyclopropylene | CHCl | 4-Methylphenyl | |
| 613 | Cyclopropylene | CHCl | 2,4-Dimethylphenyl | |
| 614 | Cyclopropylene | CHCl | 2,6-Dimethylphenyl | |
| 615 | Cyclopropylene | CHCl | 2,4,6-Trimethylphenyl | |
| 616 | Cyclopropylene | CHCl | 4-tert. Butylphenyl | |
| 617 | Cyclopropylene | CHCl | 1-Naphthyl | |
| 618 | Cyclopropylene | CHCl | 2-Naphthyl | |
| 619 | Cyclopropylene | CHCl | 4-Biphenyl | |
| 620 | Cyclopropylene | CHCl | 2-Fluorophenyl | |
| 621 | Cyclopropylene | CHCl | 4-Fluorophenyl | |
| 622 | Cyclopropylene | CHCl | 2,4-Difluorophenyl | |
| 623 | Cyclopropylene | CHCl | 2-Chlorophenyl | |
| 624 | Cyclopropylene | CHCl | 3-Chlorophenyl | |
| 625 | Cyclopropylene | CHCl | 4-Chlorophenyl | |
| 626 | Cyclopropylene | CHCl | 2,4-Dichlorophenyl | |
| 627 | Cyclopropylene | CHCl | 3,4-Dichlorophenyl | |
| 628 | Cyclopropylene | CHCl | 2-Chloro-4-fluorophenyl | |
| 629 | Cyclopropylene | CHCl | 2-Trifluoromethylphenyl | |
| 630 | Cyclopropylene | CHCl | 4-Trifluoromethylphenyl | |
| 631 | Cyclopropylene | CHCl | 4-Methoxyphenyl | |
| 632 | Cyclopropylene | CHCl | 3,4-Dimethoxyphenyl | |
| 633 | Cyclopropylene | CHCl | 4-Tetrafluoroethoxyphenyl | |
| 634 | Cyclopropylene | CHCl | 4-Trifluoromethoxyphenyl | |
| 635 | Cyclopropylene | CHCl | 2-Chloro-4-(4'-chlorophenoxy)phenyl | |
| 636 | Cyclopropylene | CHCl | 4-Phenoxyphenyl | |
| 637 | Cyclopropylene | CHCl | 4-(4'-Chlorophenoxy)phenyl | |
| 638 | Cyclopropylene | CHCl | 4-Benzyloxyphenyl | |
| 639 | Cyclopentylene | CHCl | Phenyl | |
| 640 | Cyclopentylene | CHCl | 2-Methylphenyl | |
| 641 | Cyclopentylene | CHCl | 4-Methylphenyl | |
| 642 | Cyclopentylene | CHCl | 2,4-Dimethylphenyl | |
| 643 | Cyclopentylene | CHCl | 2,6-Dimethylphenyl | |

TABLE-continued

| No. | A | B | Ar | Phys. data IR, cm$^{-1}$ |
|---|---|---|---|---|
| 644 | Cyclopentylene | CHCl | 2,4,6-Trimethylphenyl | |
| 645 | Cyclopentylene | CHCl | 4-tert. Butylphenyl | |
| 646 | Cyclopentylene | CHCl | 1-Naphthyl | |
| 647 | Cyclopentylene | CHCl | 2-Naphthyl | |
| 648 | Cyclopentylene | CHCl | 4-Biphenyl | |
| 649 | Cyclopentylene | CHCl | 2-Fluorophenyl | |
| 650 | Cyclopentylene | CHCl | 4-Fluorophenyl | oil 2959, 1606, 1510, 1478, 1423, 1228 |
| 651 | Cyclopentylene | CHCl | 2,4-Difluorophenyl | |
| 652 | Cyclopentylene | CHCl | 2-Chlorophenyl | |
| 653 | Cyclopentylene | CHCl | 3-Chlorophenyl | |
| 654 | Cyclopentylene | CHCl | 4-Chlorophenyl | oil 2959, 2873, 1492, 1478, 1423, 1408 |
| 655 | Cyclopentylene | CHCl | 2,4-Dichlorophenyl | |
| 656 | Cyclopentylene | CHCl | 3,4-Dichlorophenyl | |
| 657 | Cyclopentylene | CHCl | 2-Chloro-4-fluorophenyl | |
| 658 | Cyclopentylene | CHCl | 2-Trifluoromethylphenyl | |
| 659 | Cyclopentylene | CHCl | 4-Trifluoromethylphenyl | |
| 660 | Cyclopentylene | CHCl | 4-Methoxyphenyl | |
| 661 | Cyclopentylene | CHCl | 3,4-Dimethoxyphenyl | |
| 662 | Cyclopentylene | CHCl | 4-Tetrafluoroethoxyphenyl | |
| 663 | Cyclopentylene | CHCl | 4-Trifluoromethoxyphenyl | |
| 664 | Cyclopentylene | CHCl | 2-Chloro-4-(4'-chlorophenoxy)phenyl | |
| 665 | Cyclopentylene | CHCl | 4-Phenoxyphenyl | |
| 666 | Cyclopentylene | CHCl | 4-(4'-Chlorophenoxy)phenyl | |
| 667 | Cyclopentylene | CHCl | 4-Benzyloxyphenyl | |
| 668 | Cyclohexylene | CHCl | Phenyl | 230° C. |
| 669 | Cyclohexylene | CHCl | 2-Methylphenyl | |
| 670 | Cyclohexylene | CHCl | 4-Methylphenyl | 213-216° C. |
| 671 | Cyclohexylene | CHCl | 2,4-Dimethylphenyl | |
| 672 | Cyclohexylene | CHCl | 2,6-Dimethylphenyl | |
| 673 | Cyclohexylene | CHCl | 2,4,6-Trimethylphenyl | |
| 674 | Cyclohexylene | CHCl | 4-tert. Butylphenyl | |
| 675 | Cyclohexylene | CHCl | 1-Naphthyl | |
| 676 | Cyclohexylene | CHCl | 2-Naphthyl | |
| 677 | Cyclohexylene | CHCl | 4-Biphenyl | |
| 678 | Cyclohexylene | CHCl | 2-Fluorophenyl | |
| 679 | Cyclohexylene | CHCl | 4-Fluorophenyl | 170-173° C. |
| 680 | Cyclohexylene | CHCl | 2,4-Difluorophenyl | |
| 681 | Cyclohexylene | CHCl | 2-Chlorophenyl | |
| 682 | Cyclohexylene | CHCl | 3-Chlorophenyl | |
| 683 | Cyclohexylene | CHCl | 4-Chlorophenyl | 163° C. |
| 684 | Cyclohexylene | CHCl | 2,4-Dichlorophenyl | |
| 685 | Cyclohexylene | CHCl | 3,4-Dichlorophenyl | |
| 686 | Cyclohexylene | CHCl | 2-Chloro-4-fluorophenyl | |
| 687 | Cyclohexylene | CHCl | 2-Trifluoromethylphenyl | |
| 688 | Cyclohexylene | CHCl | 4-Trifluoromethylphenyl | |
| 689 | Cyclohexylene | CHCl | 4-Methoxyphenyl | |
| 690 | Cyclohexylene | CHCl | 3,4-Dimethoxyphenyl | |
| 691 | Cyclohexylene | CHCl | 4-Tetrafluoroethoxyphenyl | |
| 692 | Cyclohexylene | CHCl | 4-Trifluoromethoxyphenyl | |
| 693 | Cyclohexylene | CHCl | 2-Chloro-4-(4'-chlorophenoxy)phenyl | |
| 694 | Cyclohexylene | CHCl | 4-Phenoxyphenyl | |
| 695 | Cyclohexylene | CHCl | 4-(4'-Chlorophenoxy)phenyl | |
| 696 | Cyclohexylene | CHCl | 4-Benzyloxyphenyl | |
| 697 | C(CH$_3$)(C$_3$H$_7$) | CHCl | Phenyl | |
| 698 | C(CH$_3$)(C$_3$H$_7$) | CHCl | 2-Methylphenyl | |
| 699 | C(CH$_3$)(C$_3$H$_7$) | CHCl | 4-Methylphenyl | |
| 700 | C(CH$_3$)(C$_3$H$_7$) | CHCl | 2,4-Dimethylphenyl | |
| 701 | C(CH$_3$)(C$_3$H$_7$) | CHCl | 2,6-Dimethylphenyl | |
| 702 | C(CH$_3$)(C$_3$H$_7$) | CHCl | 2,4,6-Trimethylphenyl | |
| 703 | C(CH$_3$)(C$_3$H$_7$) | CHCl | 4-tert. Butylphenyl | |
| 704 | C(CH$_3$)(C$_3$H$_7$) | CHCl | 1-Naphthyl | |
| 705 | C(CH$_3$)(C$_3$H$_7$) | CHCl | 2-Naphthyl | |
| 706 | C(CH$_3$)(C$_3$H$_7$) | CHCl | 4-Biphenyl | |
| 707 | C(CH$_3$)(C$_3$H$_7$) | CHCl | 2-Fluorophenyl | |
| 708 | C(CH$_3$)(C$_3$H$_7$) | CHCl | 4-Fluorophenyl | |
| 709 | C(CH$_3$)(C$_3$H$_7$) | CHCl | 2,4-Difluorophenyl | |
| 710 | C(CH$_3$)(C$_3$H$_7$) | CHCl | 2-Chlorophenyl | |
| 711 | C(CH$_3$)(C$_3$H$_7$) | CHCl | 3-Chlorophenyl | |
| 712 | C(CH$_3$)(C$_3$H$_7$) | CHCl | 4-Chlorophenyl | |
| 713 | C(CH$_3$)(C$_3$H$_7$) | CHCl | 2,4-Dichlorophenyl | |
| 714 | C(CH$_3$)(C$_3$H$_7$) | CHCl | 3,4-Dichlorophenyl | |
| 715 | C(CH$_3$)(C$_3$H$_7$) | CHCl | 2-Chloro-4-fluorophenyl | |
| 716 | C(CH$_3$)(C$_3$H$_7$) | CHCl | 2-Trifluoromethylphenyl | |
| 717 | C(CH$_3$)(C$_3$H$_7$) | CHCl | 4-Trifluoromethylphenyl | |
| 718 | C(CH$_3$)(C$_3$H$_7$) | CHCl | 4-Methoxyphenyl | |
| 719 | C(CH$_3$)(C$_3$H$_7$) | CHCl | 3,4-Dimethoxyphenyl | |
| 720 | C(CH$_3$)(C$_3$H$_7$) | CHCl | 4-Tetrafluoroethoxyphenyl | |
| 721 | C(CH$_3$)(C$_3$H$_7$) | CHCl | 4-Trifluoromethoxyphenyl | |
| 722 | C(CH$_3$)(C$_3$H$_7$) | CHCl | 2-Chloro-4-(4'-chlorophenoxy)phenyl | |
| 723 | C(CH$_3$)(C$_3$H$_7$) | CHCl | 4-Phenoxyphenyl | |
| 724 | C(CH$_3$)(C$_3$H$_7$) | CHCl | 4-(4'-Chlorophenoxy)phenyl | |

TABLE-continued

| No. | A | B | Ar | Phys. data IR, cm$^{-1}$ |
|---|---|---|---|---|
| 725 | C(CH$_3$)(C$_3$H$_7$) | CHCl | 4-Benzyloxyphenyl | |
| 726 | C(C$_2$H$_5$)(n-C$_4$H$_9$) | CHCl | Phenyl | |
| 727 | C(C$_2$H$_5$)(n-C$_4$H$_9$) | CHCl | 2-Methylphenyl | |
| 728 | C(C$_2$H$_5$)(n-C$_4$H$_9$) | CHCl | 4-Methylphenyl | |
| 729 | C(C$_2$H$_5$)(n-C$_4$H$_9$) | CHCl | 2,4-Dimethylphenyl | |
| 730 | C(C$_2$H$_5$)(n-C$_4$H$_9$) | CHCl | 2,6-Dimethylphenyl | |
| 731 | C(C$_2$H$_5$)(n-C$_4$H$_9$) | CHCl | 2,4,6-Trimethylphenyl | |
| 732 | C(C$_2$H$_5$)(n-C$_4$H$_9$) | CHCl | 4-tert. Butylphenyl | |
| 733 | C(C$_2$H$_5$)(n-C$_4$H$_9$) | CHCl | 1-Naphthyl | |
| 734 | C(C$_2$H$_5$)(n-C$_4$H$_9$) | CHCl | 2-Naphthyl | |
| 735 | C(C$_2$H$_5$)(n-C$_4$H$_9$) | CHCl | 4-Biphenyl | |
| 736 | C(C$_2$H$_5$)(n-C$_4$H$_9$) | CHCl | 2-Fluorophenyl | |
| 737 | C(C$_2$H$_5$)(n-C$_4$H$_9$) | CHCl | 4-Fluorophenyl | |
| 738 | C(C$_2$H$_5$)(n-C$_4$H$_9$) | CHCl | 2,4-Difluorophenyl | |
| 739 | C(C$_2$H$_5$)(n-C$_4$H$_9$) | CHCl | 2-Chlorophenyl | |
| 740 | C(C$_2$H$_5$)(n-C$_4$H$_9$) | CHCl | 3-Chlorophenyl | |
| 741 | C(C$_2$H$_5$)(n-C$_4$H$_9$) | CHCl | 4-Chlorophenyl | |
| 742 | C(C$_2$H$_5$)(n-C$_4$H$_9$) | CHCl | 2,4-Dichlorophenyl | |
| 743 | C(C$_2$H$_5$)(n-C$_4$H$_9$) | CHCl | 3,4-Dichlorophenyl | |
| 744 | C(C$_2$H$_5$)(n-C$_4$H$_9$) | CHCl | 2-Chloro-4-fluorophenyl | |
| 745 | C(C$_2$H$_5$)(n-C$_4$H$_9$) | CHCl | 2-Trifluoromethylphenyl | |
| 746 | C(C$_2$H$_5$)(n-C$_4$H$_9$) | CHCl | 4-Trifluoromethylphenyl | |
| 747 | C(C$_2$H$_5$)(n-C$_4$H$_9$) | CHCl | 4-Methoxyphenyl | |
| 748 | C(C$_2$H$_5$)(n-C$_4$H$_9$) | CHCl | 3,4-Dimethoxyphenyl | |
| 749 | C(C$_2$H$_5$)(n-C$_4$H$_9$) | CHCl | 4-Tetrafluoroethoxyphenyl | |
| 750 | C(C$_2$H$_5$)(n-C$_4$H$_9$) | CHCl | 4-Trifluoromethoxyphenyl | |
| 751 | C(C$_2$H$_5$)(n-C$_4$H$_9$) | CHCl | 2-Chloro-4-(4'-chlorophenoxy)-phenyl | |
| 752 | C(C$_2$H$_5$)(n-C$_4$H$_9$) | CHCl | 4-Phenoxyphenyl | |
| 753 | C(C$_2$H$_5$)(n-C$_4$H$_9$) | CHCl | 4-(4'-Chlorophenoxy)phenyl | |
| 754 | C(C$_2$H$_5$)(n-C$_4$H$_9$) | CHCl | 4-Benzyloxyphenyl | |
| 755 | CH(tert.C$_4$H$_9$) | CHCl | Phenyl | |
| 756 | CH(tert.C$_4$H$_9$) | CHCl | 2-Methylphenyl | |
| 757 | CH(tert.C$_4$H$_9$) | CHCl | 4-Methylphenyl | |
| 758 | CH(tert.C$_4$H$_9$) | CHCl | 2,4-Dimethylphenyl | |
| 759 | CH(tert.C$_4$H$_9$) | CHCl | 2,6-Dimethylphenyl | |
| 760 | CH(tert.C$_4$H$_9$) | CHCl | 2,4,6-Trimethylphenyl | |
| 761 | CH(tert.C$_4$H$_9$) | CHCl | 4-tert. Butylphenyl | |
| 762 | CH(tert.C$_4$H$_9$) | CHCl | 1-Naphthyl | |
| 763 | CH(tert.C$_4$H$_9$) | CHCl | 2-Naphthyl | |
| 764 | CH(tert.C$_4$H$_9$) | CHCl | 4-Biphenyl | |
| 765 | CH(tert.C$_4$H$_9$) | CHCl | 2-Fluorophenyl | |
| 766 | CH(tert.C$_4$H$_9$) | CHCl | 4-Fluorophenyl | |
| 767 | CH(tert.C$_4$H$_9$) | CHCl | 2,4-Difluorophenyl | |
| 768 | CH(tert.C$_4$H$_9$) | CHCl | 2-Chlorophenyl | |
| 769 | CH(tert.C$_4$H$_9$) | CHCl | 3-Chlorophenyl | |
| 770 | CH(tert.C$_4$H$_9$) | CHCl | 4-Chlorophenyl | |
| 771 | CH(tert.C$_4$H$_9$) | CHCl | 2,4-Dichlorophenyl | |
| 772 | CH(tert.C$_4$H$_9$) | CHCl | 3,4-Dichlorophenyl | |
| 773 | CH(tert.C$_4$H$_9$) | CHCl | 2-Chloro-4-fluorophenyl | |
| 774 | CH(tert.C$_4$H$_9$) | CHCl | 2-Trifluoromethylphenyl | |
| 775 | CH(tert.C$_4$H$_9$) | CHCl | 4-Trifluoromethylphenyl | |
| 776 | CH(tert.C$_4$H$_9$) | CHCl | 4-Methoxyphenyl | |
| 777 | CH(tert.C$_4$H$_9$) | CHCl | 3,4-Dimethoxyphenyl | |
| 778 | CH(tert.C$_4$H$_9$) | CHCl | 4-Tetrafluoroethoxyphenyl | |
| 779 | CH(tert.C$_4$H$_9$) | CHCl | 4-Trifluoromethoxyphenyl | |
| 780 | CH(tert.C$_4$H$_9$) | CHCl | 2-Chloro-4-(4'-chlorophenoxy)phenyl | |
| 781 | CH(tert.C$_4$H$_9$) | CHCl | 4-Phenoxyphenyl | |
| 782 | CH(tert.C$_4$H$_9$) | CHCl | 4-(4'-Chlorophenoxy)phenyl | |
| 783 | CH(tert.C$_4$H$_9$) | CHCl | 4-Benzyloxyphenyl | |
| 784 | C(CH$_3$)$_2$ | CHOH | 3-Methylphenyl | 86–88° C. |
| 785 | C(CH$_3$)$_2$ | CHOH | 2-Methoxyphenyl | 128–130° C. |
| 786 | C(CH$_3$)$_2$ | CHOH | 3-Fluorophenyl | 3200, 2965, 1589, 1480, 1046 |
| 787 | C(CH$_3$)$_2$ | CHOH | 4-Isopropylphenyl | 97–98° C. |
| 788 | C(C$_2$H$_5$)$_2$ | CHOH | 3-Methylphenyl | 3200, 2963, 1424, 1030, 716 |
| 789 | C(C$_2$H$_5$)$_2$ | CHOH | 3-Trifluoromethylphenyl | 117–119° C. |
| 790 | C(C$_2$H$_5$)$_2$ | CHOH | 2-Methoxyphenyl | 3200, 2962, 1488, 1238, 1030, 755 |
| 791 | C(C$_2$H$_5$)$_2$ | CHOH | 3-Fluorophenyl | 3200, 2966, 1589, 1480, 1258 |
| 792 | Cyclopentylene | CHOH | 3-Trifluoromethylphenyl | 3200, 2956, 1329, 1163, 708 |
| 793 | Cyclopentylene | CHOH | 3-Methylphenyl | 3236, 2952, 1425, 1030, 717 |
| 794 | Cyclopentylene | CHOH | 2-Methoxyphenyl | 94–98° C. |
| 795 | Cyclopentylene | CHOH | 4-tert.-Butylphenyl | 106–108° C. |
| 796 | Cyclopentylene | CHOH | 3-Fluorophenyl | 3200, 2954, 1588, 1030, 717 |
| 797 | Cyclopentylene | CHOH | 4-Isopropylphenyl | 3227, 2957, 1424, 1030, 717 |
| 798 | Cyclohexylene | CHOH | 3-Methylphenyl | 137–139° C. |
| 799 | Cyclohexylene | CHOH | 4-Isopropylphenyl | 98–100° C. |
| 800 | Cyclohexylene | CHOH | 3-Trifluoromethylphenyl | 3180, 2931, 1510, 1244, 1038, 713 |
| 801 | Cyclohexylene | CHOH | 2-Methoxyphenyl | 141–142° C. |
| 802 | Cyclohexylene | CHOH | 3-Fluorophenyl | 146–148° C. |
| 803 | C(CH$_3$)$_2$ | CHCl | 3-Methylphenyl | 144–146° C. |
| 804 | C(CH$_3$)$_2$ | CHCl | 3-Fluorophenyl | 165–167° C. |
| 805 | C(CH$_3$)$_2$ | CHCl | 4-Isopropylphenyl | 104–108° C. |

TABLE-continued

| No. | A | B | Ar | Phys. data IR, cm$^{-1}$ |
|---|---|---|---|---|
| 806 | C(C$_2$H$_5$)$_2$ | CHCl | 3-Trifluoromethylphenyl | 66–69° C. |
| 807 | C(C$_2$H$_5$)$_2$ | CHCl | 3-Fluorophenyl | 205–207° C. |
| 808 | C(C$_2$H$_5$)$_2$ | CHCl | 3-Methylphenyl | 107–110° C. |
| 809 | C(C$_2$H$_5$)$_2$ | CHCl | 2-Methoxyphenyl | 83° C. |
| 810 | Cyclopentylene | CHCl | 2-Methoxyphenyl | 142–143° C. |
| 811 | C(CH$_3$)$_2$ | C=NOCH$_3$ | 4-Chlorophenyl | 47–49° C. |
| 812 | C(CH$_3$)$_2$ | C=NOCH$_3$ | 4-Methylphenyl | 159–161° C. |
| 813 | C(CH$_3$)$_2$ | C=NOCH$_3$ | 4-Fluorophenyl | 2970, 1507, 1423, 1224, 1067 |
| 814 | Cyclopentylene | C=NOCH$_3$ | 4-Fluorophenyl | 138–140° C. |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, cots, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphgaerotheca fuliginea* in cucurbits,
*Podosphaera leucotricha* in applies,
*Uncinula necator* in vines,
Puccinia species in cereals,
*Rhizoctonia solani* in cotton and lawns,
Ustilago species in ceraisland suga cane,
*Venturia inaequalis (scab)* in applies,
Helminthosporium species in cereals,
*Septoria nodorum* in wheat,
*Botrytis cinerea* (gray mold) in strawberries and grapes,
*Cersospora arachidicola* in ground nuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi. Either the fungi, or the plants, seed or materials to be protected against fungus attack, or the soil, are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkylsulfonates and aryl sulfonates); and dispersants such as ligninsulfite waste liquors and methylcellulose.

The fungicides generally contain from 0.1 to 95, and preferably from 0.5 to 90, wt. % of active ingredient. The application rates are from 0.02 to 3 kg or more of active ingredient per hectare, depending on the type of effect desired. The novel compounds may also be used for protecting materials, e.g., against Paecilomyces variotii. When the active ingredients are used for treating seed, generally amounts of from 0.001 to 50, and preferably from 0.01 to 10, g per kg of seed are required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 1 and 10 parts by weight of N-methyl-α-pyrrolidone, which is suitable for application in the form of very fine drops.

II. A mixture of 20 parts by weight of compound no. 3, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 12, 40 parts by weight of cyclohexanone, 30 parts by weight of isobutanol, 20 parts by weight of the adduct of 40 moles of ethylene oxide and 1 mole of castor oil. By finely dispersing the mixture of water, an aqueous dispersion is obtained.

IV. An aqueous dispersion of 20 parts by weight of compound no. 16, 25 parts by weight of cyclohexanol, 65 parts by weight of a mineral oil fraction having a boiling point between 210 and 280° C., and 10 parts by weight of the adduct of 40 moles of ethylene oxide and 1 mole of castor oil. By pouring the solution into water and finely distributing it therein, an aqueous dispersion is obtained.

V. A hammer-milled mixture of 80 parts by weight of compound no. 30, 3 parts by weight of the sodium salt of diisobutylnaphthalene-α-sulfonic acid, 10 pats by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 32 and 97 parts by weight of particulate kaolin. The dust contains 3 wt. % of the active ingredient.

VII. An intimate mixture of 30 parts by weight of compound no. 41, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 45, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 61, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

The active ingredient used for comparison purposes was 1-phenyl-3-(3-pyridinyl)-propan-1-one (A) disclosed in J. Org. Chem., Vol. 43 (1978), p. 3396.

Use Example 1

Action on *Alternaria solani*

Potted tomato plants of the "Große Fleischtomat" variety grown in the greenhouse were sprayed to runoff at the 4-leaf stage with aqueous suspensions containing (dry basis) 80% of active ingredient and 20% of emulsifier. After the sprayed-on layer had dried, the leaves were inoculated with an aqueous spore suspension of the fungus Alternaria solani. These plants were then placed in a water vapor-saturated chamber at from 22 to 24° C. After 4 days, the disease had spread on the untreated but inoculated plants to such a great extent that the fungicidal action of the compounds was able to be assessed.

The results show that active ingredients 1, 3, 12, 16, 30, 32, 41, 45, 61, 74, 117, 119, 128, 132, 133, 161, 175, 177, 186, 204, 206, 215 and 219, applied as 0.05 wt. % spray liquors, have a better fungicidal action (95%) than prior art comparative active ingredient A (10%).

Use Example 2

Action on *Botrytis cinerea* in paprika

Paprika seedlings of the "Neusideler Ideal Elite" variety were sprayed, after 4 to 5 leaves were well developed, to runoff with aqueous suspensions containing (dry basis) 80% of active ingredient ad 20% of emulsifier. After the sprayed-on layer had dried, the plants were sprinkled with a conidial suspension of the fungus Botrytis cinerea, and placed at 22 to 24°° C. in a chamber of high humidity. After 5 days, the disease had spread to such a great extent on the untreated plants that the necroses covered the major portion of the leaves.

The results show that active ingredients 3, 16, 32, 45, 59, 61, 70, 132, 133, 177, 190, 206, 215 and 219, applied as 0.05 wt. % spray liquors, have a better fungicidal action (95%) than prior art comparative agent A (30%).

Use Example 3

Action on *Pyrenophora teres*

Leaves of pot-grown barley seedlings of the "Igri" variety were sprayed to runoff at the two-leaf stage with aqueous suspensions containing (dry basis) 80% of active ingredient and 20% of emulsifier. After 24 hours the plants were inoculated with a spore suspension of the fungus Pyrenophora teres, and set up in high-humidity climatic cabinet at 18° C. The plants were then cultivated for a further 5 days at 20 to 22° C. and a relative humidity of 70%. The extent of leaf attack was then assessed.

The results show that active ingredients 1, 3, 12, 16, 32, 45, 61, 70, 74, 117, 119, 128, 132, 133, 157, 161, 177, 186, 204, 206, 215, 219, 650 and 683, applied as 0.05 wt % spray liquors, have a better fungicidal action (95%) than prior art comparative agent A (30%).

We claim:

1. A member selected from the group consisting of a β-picoline derivative of the formula

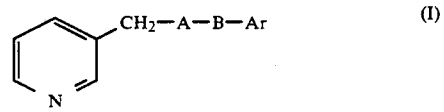

where
A is $CR^1R^2$,
$R^1$ and $R^2$ independently of one another are each hydrogen, $C_1$-$C_6$-alkyl, $C_2$-$C_6$-alkenyl or $C_2$-$C_6$-alkynyl or $R^1$ and $R^2$ together form a methylene chain having from 2 to 6 methylene groups,
B is one of the groups of $CH_2$, $CHOR^3$, $CHR^4$, C=O or C=N—O—$R^5$, $R^3$ is hydrogen, $C_1$-$Ch_6$-alkyl, $C_1$-$C_6$-haloalkyl, $C_3$-$C_8$-cycloalkyl, $C_3$-$C_6$-alkenyl, $C_2$-$C_6$-acyl, phenyl, benzyl or benzoyl, where the phenyl ring may be unsubstituted or substituted by from one to three substituents selected from the group consisting of $C_1$-$C_4$-alkyl, $C_1$-$C_4$-alkoxy, $C_1$-$C_4$-haloalkyl, $C_1C_4$-haloalkoxy, halogen, cyano and nitro, $R^4$ is fluorine, chlorine, bromine or iodine, $R^5$ is hydrogen, $C_1$-$C_6$-alkyl, $C_1$-$C_6$-haloalkyl, $C_3$-$C_7$-cycloalkyl, $C_3$-$C_6$-alkenyl or aralkyl where the alkyl radical is of 1 to 4 carbon atoms and the aryl radical may be unsubstituted or substituted by from one to three substituents selected from the groups consisting of $C_1$-$C_4$-alkyl, $C_1$-$C_4$-alkoxy, $C_1$-$C_4$-haloalkyl, halogen, cycano and nitro, and Ar is a phenyl or naphthyl radical which is unsubstituted or monosubstituted to trisubstituted by halogen, $C_1$-$C_6$-alkyl, $C_1$-$C_4$-alkoxy, $C_1$-$C_4$-haloalkyl, $C_1$-$C_4$-haloalkoxy, phenyl, phenoxy, halophenyl, halophenoxy or benzyloxy,
its N-oxides and plant-tolerated acid addition salts, except for the compound in which A is $CH_2$, B is C=O and Ar is phenyl.

2. A fungicidal composition containing an inert carrier and a fungicidal amount of a β-picoline derivative of the formula

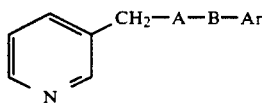

where
A is $CR^1R^2$
R$^1$ and R$^2$ independently of one another are each hydrogen, $C_1$-$C_6$-alkyl, $C_2$-$C_6$-alkenyl or $C_2$-$C_6$-alkynyl or R$^1$ and R$^2$ together form a methylene chain having from 2 to 6 methylene groups, B is one of the groups of $C_2$, $CHOR^3$, $CHR^4$, $C=O$ or $C=N-O-R^5$, R$^3$ is hydrogen, $C_1$-$C_6$-alkyl, $C_1$-$C_6$-haloalkyl, $C_3$-$C_8$-cycloalkyl, $C_3$-$C_6$-alkenyl, $C_2$-$C_6$-acyl, phenyl, benzyl or benzoyl, where the phenyl ring may be unsubstituted or substituted by from one to three substituents selected from the group consisting of $C_1$-$C_4$-alkyl, $C_1$-$C_4$-alkoxy, $C_1$-$C_4$-haloalkyl, $C_1$-$C_4$-haloalkoxy, halogen, cyano and nitro, R$^4$ is fluorine, chlorine, bromine or iodine, R$^5$ is hydrogen, $C_1$-$C_6$-alkyl, Chd 1-$C_6$-haloalkyl, $C_3$-$C_7$-cycloalkyl, $C_3$-$C_6$-alkenyl or aralkyl where the alkyl radical is of 1 to 4 carbon atoms and the aryl radical may be unsubstituted or substituted by from one to three substituents selected from the groups consisting of $C_1$-$C_4$-alkyl, $C_1$-$C_4$-alkoxy, $C_1$-$C_4$-haloalkyl, halogen, cyano and nitro, and Ar is a phenyl or naphthyl radical which is unsubstituted or monosubstituted to trisubstituted by halogen, $C_1$-$C_6$-alkyl, $C_1$-$C_4$-alkoxy, $C_1$-$C_4$-haloalkyl, $C_1$-$C_4$-haloalkoxy, phenyl, phenoxy, halophenyl, halophenoxy or benzyloxy, or its N-oxide or plant-tolerated acid addition salt, except for the compound in which A is $CH_2$, B is $C=O$ and Ar is phenyl.

3. A method for controlling fungi, wherein the fungi or the materials, plants, soils or seeds threatened by fungal attack are treated with a fungicidal amount of a β-picoline derivative of the formula I

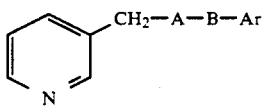

where
A is $CR^1R^2$.
R$^1$ and R$^2$ independently of one another are each hydrogen, $C_1$-$C_6$-alkyl, $C_2$-$C_6$-alkenyl or $C_2$-$C_6$-alkynyl or R$^1$ and R$^2$ together form a methylene chain having from 2 to 6 methylene groups, B is one of the groups $CH_2$, $CHOR^3$, $CHR^4$, $C=O$ or $C=N-O-R^5$, R$^3$ is hydrogen, $C_1$-$C_6$-alkyl, $C_1$-$C_6$-haloalkyl, $C_3$-$C_8$-cycloalkyl, $C_3$-$C_6$-alkenyl, $C_2$-$C_6$-acyl, phenyl, benzyl or benzoyl, where the phenyl ring maybe unsubstituted or substituted by from one to three substituents selected from the group consisting of $C_1$-$C_4$-alkyl, $C_1$-$C_4$-alkoxy, $C_1$-$C_4$-haloalkyl, $C_1$-$C_4$-haloalkoxy, halogen, cyano and nitro, R$^4$ is fluorine, chlorine, bromine or iodine, R$^5$ is hydrogen, $C_1$-$C_6$-alkyl, $C_1$-$C_6$-haloalkyl, $C_3$-$C_7$-cycloalkyl, $C_3$-$C_6$-alkenyl or aralkyl where the alkyl radical is of 1 to 4 carbon atoms and the aryl radical may be unsubstituted or substituted by from one to three substituents selected from the group consisting of $C_1$-$C_4$-alkyl, $C_1$-$C_4$-alkoxy, $C_1$-$C_4$-haloalkyl, halogen, cyano and nitro, and Ar is a phenyl or naphthyl radical which is unsubstituted or substituted by from one to three substituents selected from the group consisting of $C_1$-$C_4$-alkyl, $C_1$-$C_4$-alkoxy, $C_1$-$C_4$-haloalkyl, halogen, cyano and nitro, and Ar is a phenyl or naphthyl radical which is unsubstituted or monosubstituted to trisubstituted by halogen, $C_1$-$C_6$-alkyl, $C_1$-$C_4$-alkoxy, $C_1$-$C_4$-haloalkyl, $C_1$-$C_4$-haloalkoxy, phenyl, phenoxy, halophenyl, halophenoxy or benzyloxy, or its N-oxide or plant-tolerated acid addition salt.

4. A compound as claimed in claim 1, wherein A is $C(C_2H_5)_2$, B is $C=O$ and Ar is 4-fluorophenyl.

5. A compound as claimed in claim 1, wherein A is $C(C_2H_5)_2$, B is CHCl and Ar is 4-fluorophenyl.

6. A compound as claimed in claim 1, wherein B is $C=O$.

7. A compound as claimed in claim 1, wherein B is CHOH.

8. A compound as claimed in claim 1, wherein B is CHCl.

9. A compound as claimed in claim 1, wherein B is $C=NOR^5$.

10. A compound as claimed in claim 1, wherein A is cyclopentylene, B is CHOH, and Ar is 4-iopropylphenyl.

* * * * *